US011944524B2

(12) United States Patent
Schneider et al.

(10) Patent No.: US 11,944,524 B2
(45) Date of Patent: Apr. 2, 2024

(54) METHODS AND APPARATUSES FOR MAKING ELASTOMERIC LAMINATES

(71) Applicant: The Procter & Gamble Company, Cincinnati, OH (US)

(72) Inventors: Uwe Schneider, Cincinnati, OH (US); Joseph Allen Eckstein, Sunman, IN (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 18/111,107

(22) Filed: Feb. 17, 2023

(65) Prior Publication Data

US 2023/0190538 A1 Jun. 22, 2023

Related U.S. Application Data

(63) Continuation of application No. 17/409,850, filed on Aug. 24, 2021, now Pat. No. 11,607,348, which is a
(Continued)

(51) Int. Cl.
*A61F 13/00* (2006.01)
*A61F 13/15* (2006.01)
(Continued)

(52) U.S. Cl.
CPC .. *A61F 13/15601* (2013.01); *A61F 13/15593* (2013.01); *A61F 13/15699* (2013.01);
(Continued)

(58) Field of Classification Search
CPC .......... A61F 13/00; A61F 13/10; A61F 13/15; A61F 13/155; A61F 13/1559;
(Continued)

(56) References Cited

U.S. PATENT DOCUMENTS 3,113,225 A 12/1963 Claus
3,434,189 A 3/1969 Buck et al.
(Continued)

FOREIGN PATENT DOCUMENTS

CA 2158790 A1 3/1996
CN 1257442 A 6/2000
(Continued)

OTHER PUBLICATIONS

PCT Search Report and Written Opinion for PCT/US2018/048443 dated Oct. 26, 2018, 10 pages.
(Continued)

*Primary Examiner* — Jacob T Minskey
*Assistant Examiner* — Matthew Hoover
(74) *Attorney, Agent, or Firm* — Charles R. Matson

(57) ABSTRACT

The present disclosure relates to methods for making elastomeric laminates that may be used as components of absorbent articles. Aspects of the methods for assembling elastomeric laminates may utilize elastic strands supplied from beams that may be joined with first and second substrates, and may be configured to carry out various types of operations, such as bonding and splicing operations.

10 Claims, 24 Drawing Sheets

Related U.S. Application Data continuation of application No. 16/115,617, filed on Aug. 29, 2018, now Pat. No. 11,129,753.

(60) Provisional application No. 62/686,896, filed on Jun. 19, 2018, provisional application No. 62/687,031, filed on Jun. 19, 2018, provisional application No. 62/685,429, filed on Jun. 15, 2018, provisional application No. 62/581,278, filed on Nov. 3, 2017, provisional application No. 62/553,149, filed on Sep. 1, 2017, provisional application No. 62/553,538, filed on Sep. 1, 2017, provisional application No. 62/553,171, filed on Sep. 1, 2017.

(51) Int. Cl.
*A61F 13/49* (2006.01)
*B29C 65/00* (2006.01)
*B29C 65/08* (2006.01)
*B29C 65/18* (2006.01)
*B29C 65/48* (2006.01)
*B29C 65/72* (2006.01)
B29C 65/02 (2006.01)
B29L 31/48 (2006.01)

(52) U.S. Cl.
CPC .... *A61F 13/15739* (2013.01); *A61F 13/4902* (2013.01); *B29C 65/08* (2013.01); *B29C 65/086* (2013.01); *B29C 65/18* (2013.01); *B29C 65/48* (2013.01); *B29C 65/72* (2013.01); *B29C 66/1122* (2013.01); *B29C 66/43* (2013.01); *B29C 66/71* (2013.01); *B29C 66/7294* (2013.01); *B29C 66/81433* (2013.01); *B29C 66/83511* (2013.01); *A61F 2013/49025* (2013.01); *B29C 65/02* (2013.01); *B29K 2713/00* (2013.01); *B29L 2031/4878* (2013.01)

(58) Field of Classification Search
CPC .............. A61F 13/15593; A61F 13/156; A61F 13/156; A61F 13/15601; A61F 13/1569; A61F 13/15699; A61F 13/157; A61F 13/1573; A61F 13/15739; A61F 13/40; A61F 13/49; A61F 13/49; A61F 13/4902; B29C 65/00; B29C 65/08; B29C 65/086; B29C 65/10; B29C 65/18; B29C 65/40; B29C 65/48; B29C 65/70; B29C 65/72; B29C 66/00; B29C 66/10; B29C 66/11; B29C 66/112; B29C 66/1122; B29C 66/40; B29C 66/43; B29C 66/70; B29C 66/71; B29C 66/72; B29C 66/729; B29C 66/7294; B29C 66/80; B29C 66/81; B29C 66/814; B29C 66/8143; B29C 66/81433; B29C 66/83; B29C 66/835; B29C 66/8351; B29C 66/83511
See application file for complete search history.

(56) References Cited

U.S. PATENT DOCUMENTS

| | | |
|---|---|---|
| 3,508,722 A | 4/1970 | Kohl |
| 3,562,041 A | 2/1971 | Robertson |
| 3,575,782 A | 4/1971 | Hansen |
| 3,733,238 A | 5/1973 | Long |
| 3,860,003 A | 1/1975 | Buell |
| 3,871,378 A | 3/1975 | Duncan et al. |
| 4,251,587 A | 2/1981 | Mimura et al. |
| 4,333,979 A | 6/1982 | Sciaraffa |
| 4,525,905 A | 7/1985 | Bogucki-Land |
| 4,610,678 A | 9/1986 | Weisman |
| 4,640,859 A | 2/1987 | Hansen |
| 4,657,539 A | 4/1987 | Hasse |
| 4,673,402 A | 6/1987 | Weisman et al. |
| 4,695,278 A | 9/1987 | Lawson |
| 4,704,115 A | 11/1987 | Buell |
| 4,741,941 A | 5/1988 | Englebert |
| 4,776,911 A | 10/1988 | Uda et al. |
| 4,795,454 A | 1/1989 | Dragoo |
| 4,834,735 A | 5/1989 | Alemany |
| 4,854,984 A | 8/1989 | Ball |
| 4,888,231 A | 12/1989 | Angstadt |
| 4,909,803 A | 3/1990 | Aziz |
| 4,940,464 A | 7/1990 | Van |
| 4,984,584 A | 1/1991 | Hansen |
| 5,003,676 A | 4/1991 | Mcfalls |
| 5,060,881 A | 10/1991 | Bogucki-land |
| 5,092,861 A | 3/1992 | Nomura |
| 5,110,403 A | 5/1992 | Ehlert |
| 5,167,897 A | 12/1992 | Weber |
| 5,246,433 A | 9/1993 | Hasse |
| 5,334,289 A | 8/1994 | Trokhan |
| 5,342,341 A | 8/1994 | Igaue |
| 5,360,420 A | 11/1994 | Cook |
| 5,393,360 A | 2/1995 | Bridges |
| 5,413,849 A | 5/1995 | Austin |
| 5,514,523 A | 5/1996 | Trokhan |
| 5,531,729 A | 7/1996 | Coles |
| 5,552,013 A | 9/1996 | Ehlert et al. |
| 5,558,658 A | 9/1996 | Menard et al. |
| 5,562,646 A | 10/1996 | Goldman |
| 5,569,234 A | 10/1996 | Buell |
| 5,575,874 A | 11/1996 | Griesbach, III |
| 5,599,335 A | 2/1997 | Goldman |
| 5,599,420 A | 2/1997 | Yeo |
| 5,628,097 A | 5/1997 | Benson |
| 5,643,588 A | 7/1997 | Roe |
| 5,643,653 A | 7/1997 | Griesbach, III |
| 5,669,894 A | 9/1997 | Goldman |
| 5,674,216 A | 10/1997 | Buell |
| 5,702,551 A | 12/1997 | Huber |
| 5,775,380 A | 7/1998 | Roelstraete |
| 5,827,259 A | 10/1998 | Laux |
| 5,858,504 A | 1/1999 | Fitting |
| 5,887,322 A | 3/1999 | Hartzheim |
| 5,895,623 A | 4/1999 | Trokhan |
| 5,897,545 A | 4/1999 | Kline |
| 5,916,661 A | 6/1999 | Benson |
| 5,957,908 A | 9/1999 | Kline |
| 5,964,973 A | 10/1999 | Heath et al. |
| 5,968,025 A | 10/1999 | Roe |
| 5,993,433 A | 11/1999 | St. Louis |
| 5,997,521 A | 12/1999 | Robles et al. |
| 6,036,796 A | 3/2000 | Halbert |
| 6,043,168 A | 3/2000 | Colman |
| 6,107,537 A | 8/2000 | Elder |
| 6,107,539 A | 8/2000 | Palumbo |
| 6,118,041 A | 9/2000 | Roe |
| 6,120,487 A | 9/2000 | Ashton |
| 6,120,489 A | 9/2000 | Johnson |
| 6,139,941 A | 10/2000 | Jankevics |
| 6,153,209 A | 11/2000 | Vega |
| 6,248,195 B1 | 6/2001 | Schmitz |
| 6,248,197 B1 | 6/2001 | Nakanishi et al. |
| 6,291,039 B1 | 9/2001 | Combe |
| 6,319,239 B1 | 11/2001 | Daniels |
| 6,361,638 B2 | 3/2002 | Takai |
| 6,383,431 B1 | 5/2002 | Dobrin |
| 6,395,957 B1 | 5/2002 | Chen |
| 6,410,129 B2 | 6/2002 | Zhang |
| 6,426,444 B2 | 7/2002 | Roe |
| 6,475,600 B1 | 11/2002 | Morman et al. |
| 6,478,785 B1 | 11/2002 | Ashton et al. |
| 6,482,191 B1 | 11/2002 | Roe et al. |
| 6,508,641 B1 | 1/2003 | Kubik |
| 6,545,197 B1 | 4/2003 | Muller |
| 6,554,815 B1 | 4/2003 | Umebayashi |
| 6,586,652 B1 | 7/2003 | Roe |
| 6,617,016 B2 | 9/2003 | Zhang |
| 6,627,787 B1 | 9/2003 | Roe |
| 6,632,504 B1 | 10/2003 | Gillespie |

(56) References Cited

U.S. PATENT DOCUMENTS

| | | | |
|---|---|---|---|
| 6,645,330 | B2 | 11/2003 | Pargass |
| 6,673,418 | B1 | 1/2004 | Deolivera |
| 6,676,054 | B2 | 1/2004 | Heaney |
| 6,702,798 | B2 | 3/2004 | Christoffel |
| 6,790,798 | B1 | 9/2004 | Suzuki |
| 6,821,301 | B2 | 11/2004 | Azuse |
| 6,825,393 | B2 | 11/2004 | Roe |
| 6,861,571 | B1 | 3/2005 | Roe |
| 7,008,685 | B2 | 3/2006 | Groitzsch |
| 7,118,558 | B2 | 10/2006 | Wu |
| 7,465,367 | B2 | 12/2008 | Day |
| 7,513,969 | B2 | 4/2009 | Ashraf |
| 7,569,039 | B2 | 8/2009 | Matsuda |
| 7,582,348 | B2 * | 9/2009 | Ando ............... A61F 13/4902 442/328 |
| 7,585,348 | B2 | 9/2009 | Nyberg et al. |
| 7,642,398 | B2 | 1/2010 | Jaerpenberg |
| 7,708,849 | B2 | 5/2010 | Mccabe |
| 7,777,094 | B2 | 8/2010 | Mori |
| 7,861,756 | B2 | 1/2011 | Jenquin |
| 7,878,447 | B2 | 2/2011 | Hartzheim |
| 7,901,393 | B2 | 3/2011 | Matsuda |
| 7,905,446 | B2 | 3/2011 | Hartzheim |
| 7,954,213 | B2 | 6/2011 | Mizutani |
| 8,043,984 | B2 | 10/2011 | Stadelman et al. |
| 8,093,161 | B2 | 1/2012 | Bansal |
| 8,143,177 | B2 | 3/2012 | Noda |
| 8,186,296 | B2 | 5/2012 | Brown |
| 8,193,407 | B2 | 6/2012 | Mansfield et al. |
| 8,226,625 | B2 | 7/2012 | Turner |
| 8,277,430 | B2 | 10/2012 | Tabor et al. |
| 8,308,706 | B2 | 11/2012 | Fukae |
| 8,377,554 | B2 | 2/2013 | Martin |
| 8,388,594 | B2 | 3/2013 | Turner |
| 8,440,043 | B1 | 5/2013 | Schneider |
| 8,551,608 | B2 | 10/2013 | Kawakami et al. |
| 8,585,666 | B2 | 11/2013 | Weisman |
| 8,647,319 | B2 | 2/2014 | Een |
| 8,729,332 | B2 | 5/2014 | Takahashi |
| 8,778,127 | B2 | 7/2014 | Schneider |
| 8,853,108 | B2 | 10/2014 | Ahoniemi |
| 8,906,275 | B2 | 12/2014 | Davis |
| 8,939,957 | B2 | 1/2015 | Raycheck |
| 9,005,392 | B2 | 4/2015 | Schneider |
| 9,039,855 | B2 | 5/2015 | Schneider |
| 9,050,213 | B2 | 6/2015 | Lavon |
| 9,156,648 | B2 | 10/2015 | Yamamoto |
| 9,168,182 | B2 | 10/2015 | Hargett |
| 9,198,804 | B2 | 12/2015 | Nakamura |
| 9,226,861 | B2 | 1/2016 | Lavon |
| 9,248,054 | B2 | 2/2016 | Brown |
| 9,265,672 | B2 | 2/2016 | Brown |
| 9,295,590 | B2 | 3/2016 | Brown |
| 9,370,775 | B2 | 6/2016 | Harvey |
| 9,440,043 | B2 | 9/2016 | Arora |
| 9,453,303 | B2 | 9/2016 | Aberg |
| 9,539,735 | B2 | 1/2017 | Ferguson |
| 9,732,454 | B2 | 8/2017 | Davis |
| 9,758,339 | B2 | 9/2017 | Yanez, Jr. |
| 9,795,520 | B2 | 10/2017 | Kaneko |
| 9,862,174 | B2 | 1/2018 | Venkitaraman et al. |
| 9,877,876 | B2 | 1/2018 | Huang |
| 10,190,244 | B2 | 1/2019 | Ashraf |
| 10,596,045 | B2 | 3/2020 | Koshijima |
| 10,792,194 | B2 | 10/2020 | Hohm |
| 11,141,322 | B2 | 10/2021 | Schneider et al. |
| 11,147,717 | B2 | 10/2021 | Schneider et al. |
| 2001/0030014 | A1 | 10/2001 | Kwok |
| 2002/0026660 | A1 | 3/2002 | Goda |
| 2002/0046802 | A1 | 4/2002 | Tachibana |
| 2002/0072723 | A1 | 6/2002 | Ronn |
| 2002/0099347 | A1 | 7/2002 | Chen et al. |
| 2002/0103469 | A1 | 8/2002 | Chen |
| 2002/0134067 | A1 * | 9/2002 | Heaney ............... B65H 69/04 57/22 |
| 2002/0153271 | A1 | 10/2002 | Mcmanus |
| 2002/0177829 | A1 | 11/2002 | Fell |
| 2003/0044585 | A1 | 3/2003 | Taylor |
| 2003/0070780 | A1 | 4/2003 | Chen |
| 2003/0087056 | A1 | 5/2003 | Ducker |
| 2003/0089454 | A1 | 5/2003 | Johnson |
| 2003/0093045 | A1 | 5/2003 | Erdman |
| 2003/0119404 | A1 | 6/2003 | Belau |
| 2003/0125687 | A1 | 7/2003 | Gubernick et al. |
| 2003/0144643 | A1 | 7/2003 | Jarpenberg |
| 2003/0203162 | A1 | 10/2003 | Fenwick |
| 2003/0233082 | A1 | 12/2003 | Kline |
| 2004/0006323 | A1 | 1/2004 | Hall |
| 2004/0030317 | A1 | 2/2004 | Torigoshi |
| 2004/0059309 | A1 | 3/2004 | Nortman |
| 2004/0097895 | A1 | 5/2004 | Busam |
| 2004/0127881 | A1 | 7/2004 | Stevens et al. |
| 2004/0133180 | A1 | 7/2004 | Mori |
| 2004/0158212 | A1 | 8/2004 | Ponomarenko |
| 2004/0158217 | A1 | 8/2004 | Wu |
| 2004/0167493 | A1 | 8/2004 | Jarpenberg et al. |
| 2004/0219854 | A1 | 11/2004 | Groitzsch |
| 2004/0230171 | A1 | 11/2004 | Ando |
| 2005/0013975 | A1 | 1/2005 | Brock |
| 2005/0107764 | A1 | 5/2005 | Matsuda |
| 2005/0133527 | A1 | 6/2005 | Dullea et al. |
| 2005/0148971 | A1 | 7/2005 | Kuroda et al. |
| 2005/0208277 | A1 | 9/2005 | Harris |
| 2005/0230037 | A1 | 10/2005 | Jenquin |
| 2005/0244640 | A1 | 11/2005 | Riswick et al. |
| 2005/0267431 | A1 | 12/2005 | Sasaki |
| 2006/0032578 | A1 | 2/2006 | Schneider |
| 2006/0047260 | A1 | 3/2006 | Ashton |
| 2006/0069373 | A1 | 3/2006 | Schlinz |
| 2006/0087053 | A1 | 4/2006 | Odonnell |
| 2006/0105075 | A1 | 5/2006 | Otsubo |
| 2006/0137810 | A1 | 6/2006 | Beck et al. |
| 2006/0189954 | A1 | 8/2006 | Kudo |
| 2006/0228969 | A1 | 10/2006 | Erdman |
| 2006/0270302 | A1 | 11/2006 | Ando |
| 2007/0026753 | A1 | 2/2007 | Neely |
| 2007/0045143 | A1 | 3/2007 | Clough |
| 2007/0045144 | A1 | 3/2007 | Wheeler |
| 2007/0131335 | A1 | 6/2007 | Zhou |
| 2007/0141311 | A1 | 6/2007 | Mleziva |
| 2007/0179466 | A1 | 8/2007 | Tremblay |
| 2007/0196650 | A1 | 8/2007 | Yamamoto et al. |
| 2008/0134487 | A1 | 6/2008 | Hartono |
| 2008/0149292 | A1 | 6/2008 | Scherb |
| 2008/0161768 | A1 | 7/2008 | Baba |
| 2008/0287897 | A1 | 11/2008 | Guzman |
| 2009/0177176 | A1 | 7/2009 | Saito |
| 2009/0204093 | A1 | 8/2009 | Vasic |
| 2009/0312730 | A1 | 12/2009 | Lavon |
| 2010/0022151 | A1 | 1/2010 | Malowaniec |
| 2010/0036346 | A1 | 2/2010 | Hammons |
| 2010/0048072 | A1 | 2/2010 | Kauschke |
| 2010/0075103 | A1 | 3/2010 | Miyamoto |
| 2010/0076394 | A1 | 3/2010 | Hayase |
| 2010/0248575 | A1 | 9/2010 | Malz |
| 2010/0307668 | A1 | 12/2010 | Lange |
| 2011/0092943 | A1 | 4/2011 | Bishop |
| 2011/0118689 | A1 | 5/2011 | Een |
| 2011/0120897 | A1 | 5/2011 | Takahashi |
| 2011/0250378 | A1 | 10/2011 | Eaton |
| 2012/0004633 | A1 | 1/2012 | R. Marcelo |
| 2012/0061015 | A1 | 3/2012 | Lavon |
| 2012/0061016 | A1 | 3/2012 | Lavon |
| 2012/0071852 | A1 | 3/2012 | Tsang et al. |
| 2012/0095429 | A1 | 4/2012 | Kobayashi |
| 2012/0271267 | A1 | 10/2012 | Love |
| 2012/0277713 | A1 | 11/2012 | Raycheck |
| 2012/0323206 | A1 | 12/2012 | Mcmorrow |
| 2013/0032656 | A1 | 2/2013 | Yamamoto |
| 2013/0072887 | A1 | 3/2013 | Lavon |
| 2013/0102982 | A1 | 4/2013 | Nakano |
| 2013/0112584 | A1 | 5/2013 | Gaspari |
| 2013/0139960 | A1 | 6/2013 | Maruyama |
| 2013/0171421 | A1 | 7/2013 | Weisman |

(56) References Cited

U.S. PATENT DOCUMENTS

| | | |
|---|---|---|
| 2013/0199696 A1 | 8/2013 | Schneider |
| 2013/0199707 A1* | 8/2013 | Schneider ......... A61F 13/15593 156/164 |
| 2013/0211356 A1 | 8/2013 | Nishikawa |
| 2013/0211363 A1 | 8/2013 | Lavon |
| 2013/0255861 A1 | 10/2013 | Schneider |
| 2013/0255862 A1 | 10/2013 | Schneider |
| 2013/0255863 A1 | 10/2013 | Lavon |
| 2013/0255864 A1 | 10/2013 | Schneider |
| 2013/0255865 A1 | 10/2013 | Brown |
| 2013/0261589 A1 | 10/2013 | Fujkawa |
| 2013/0306226 A1 | 11/2013 | Zink |
| 2014/0000794 A1 | 1/2014 | Hamilton |
| 2014/0005621 A1 | 1/2014 | Roe |
| 2014/0018759 A1 | 1/2014 | Jayasinghe |
| 2014/0041797 A1 | 2/2014 | Schneider |
| 2014/0107605 A1 | 4/2014 | Schroer, Jr. |
| 2014/0127460 A1 | 5/2014 | Xu |
| 2014/0136893 A1 | 5/2014 | Xie et al. |
| 2014/0148773 A1 | 5/2014 | Brown |
| 2014/0234575 A1 | 8/2014 | Mitsuno |
| 2014/0235127 A1 | 8/2014 | Dejesus |
| 2014/0257231 A1 | 9/2014 | Wang |
| 2014/0276517 A1 | 9/2014 | Chester |
| 2014/0288521 A1 | 9/2014 | Wade |
| 2014/0296815 A1 | 10/2014 | Takken |
| 2014/0302286 A1 | 10/2014 | Okuda |
| 2014/0305570 A1 | 10/2014 | Matsunaga |
| 2014/0324009 A1 | 10/2014 | Lee |
| 2014/0343525 A1 | 11/2014 | Roh et al. |
| 2014/0377506 A1 | 12/2014 | Eckstein |
| 2014/0377513 A1 | 12/2014 | Galie |
| 2015/0083309 A1 | 3/2015 | Long |
| 2015/0126956 A1 | 5/2015 | Raycheck |
| 2015/0136893 A1 | 5/2015 | Koskol |
| 2015/0164708 A1 | 6/2015 | Hashimoto |
| 2015/0167207 A1 | 6/2015 | Bongartz et al. |
| 2015/0173967 A1 | 6/2015 | Kreuzer |
| 2015/0230995 A1 | 8/2015 | Kaneko |
| 2015/0245958 A1 | 9/2015 | Chmielewski |
| 2015/0257941 A1 | 9/2015 | Eckstein |
| 2015/0282999 A1 | 10/2015 | Arizti |
| 2015/0320612 A1 | 11/2015 | Seitz |
| 2015/0320613 A1 | 11/2015 | Seitz |
| 2015/0320619 A1 | 11/2015 | Seitz |
| 2015/0320620 A1 | 11/2015 | Seitz |
| 2015/0320622 A1 | 11/2015 | Seitz |
| 2015/0328056 A1 | 11/2015 | Een |
| 2015/0351972 A1 | 12/2015 | Bing-wo |
| 2016/0058624 A1 | 3/2016 | Hohm |
| 2016/0058627 A1 | 3/2016 | Barnes |
| 2016/0067119 A1 | 3/2016 | Weisman |
| 2016/0100989 A1 | 4/2016 | Seitz |
| 2016/0100997 A1 | 4/2016 | Seitz |
| 2016/0106633 A1 | 4/2016 | Nagata |
| 2016/0129661 A1 | 5/2016 | Arora |
| 2016/0136009 A1 | 5/2016 | Weisman |
| 2016/0228305 A1 | 8/2016 | Gualtieri |
| 2016/0270977 A1 | 9/2016 | Surushe et al. |
| 2016/0288407 A1 | 10/2016 | Ehlert et al. |
| 2016/0331600 A1 | 11/2016 | Polidori |
| 2017/0014281 A1 | 1/2017 | Xie |
| 2017/0027774 A1 | 2/2017 | Ashraf |
| 2017/0029993 A1 | 2/2017 | Ashraf |
| 2017/0029994 A1 | 2/2017 | Ashraf |
| 2017/0056256 A1 | 3/2017 | Smith |
| 2017/0065461 A1 | 3/2017 | Schneider |
| 2017/0079852 A1 | 3/2017 | Fujima |
| 2017/0119595 A1 | 5/2017 | Carla |
| 2017/0191198 A1 | 7/2017 | Ashraf |
| 2017/0258650 A1 | 9/2017 | Rosati |
| 2017/0281417 A1 | 10/2017 | Ishikawa |
| 2017/0319403 A1 | 11/2017 | Bewick-sonntag |
| 2017/0348163 A1 | 12/2017 | Lakso |
| 2018/0092784 A1 | 4/2018 | Wade |
| 2018/0140473 A1 | 5/2018 | Koshijima |
| 2018/0154607 A1 | 6/2018 | Mitsuno et al. |
| 2018/0168874 A1 | 6/2018 | Lavon |
| 2018/0168875 A1 | 6/2018 | Lavon |
| 2018/0168876 A1 | 6/2018 | Lavon |
| 2018/0168877 A1 | 6/2018 | Schneider |
| 2018/0168878 A1 | 6/2018 | Schneider |
| 2018/0168879 A1 | 6/2018 | Schneider |
| 2018/0168880 A1 | 6/2018 | Schneider |
| 2018/0168885 A1 | 6/2018 | Zink, II |
| 2018/0168887 A1 | 6/2018 | Lavon |
| 2018/0168888 A1 | 6/2018 | Zink |
| 2018/0168889 A1 | 6/2018 | Lavon |
| 2018/0168890 A1 | 6/2018 | Lavon |
| 2018/0168891 A1 | 6/2018 | Wise |
| 2018/0168892 A1 | 6/2018 | Lavon |
| 2018/0168893 A1 | 6/2018 | Ashraf |
| 2018/0169964 A1 | 6/2018 | Schneider |
| 2018/0170026 A1 | 6/2018 | Schneider |
| 2018/0170027 A1 | 6/2018 | Schneider |
| 2018/0214318 A1 | 8/2018 | Ashraf |
| 2018/0214321 A1 | 8/2018 | Ashraf |
| 2018/0216269 A1 | 8/2018 | Ashraf |
| 2018/0216270 A1 | 8/2018 | Ashraf |
| 2018/0216271 A1 | 8/2018 | Ashraf |
| 2018/0311398 A1 | 11/2018 | Neton et al. |
| 2018/0333311 A1 | 11/2018 | Maki |
| 2019/0003079 A1 | 1/2019 | Ashraf |
| 2019/0003080 A1 | 1/2019 | Ashraf |
| 2019/0070041 A1 | 3/2019 | Schneider |
| 2019/0070042 A1 | 3/2019 | Beck |
| 2019/0112737 A1 | 4/2019 | Ashraf |
| 2019/0246196 A1 | 8/2019 | Han |
| 2019/0254881 A1 | 8/2019 | Ishikawa |
| 2019/0298586 A1 | 10/2019 | Ashraf |
| 2019/0298587 A1 | 10/2019 | Ashraf |
| 2019/0374392 A1 | 12/2019 | Ninomiya |
| 2019/0374404 A1 | 12/2019 | Ninomiya |
| 2020/0155370 A1 | 5/2020 | Ohtsubo |
| 2020/0155371 A1 | 5/2020 | Ohtsubo |
| 2020/0206040 A1 | 7/2020 | Andrews |
| 2020/0214901 A1 | 7/2020 | Andrews |
| 2020/0298545 A1 | 9/2020 | Andrews |
| 2021/0205152 A1 | 7/2021 | Polidori et al. |
| 2021/0378878 A1 | 12/2021 | Schneider et al. |
| 2021/0401633 A1 | 12/2021 | Schneider et al. |
| 2021/0401634 A1 | 12/2021 | Schneider et al. |
| 2022/0000676 A1 | 1/2022 | Schneider et al. |

FOREIGN PATENT DOCUMENTS

| | | |
|---|---|---|
| CN | 1276196 A | 12/2000 |
| CN | 1375269 A | 10/2002 |
| CN | 1461634 A | 12/2003 |
| CN | 1685099 A | 10/2005 |
| CN | 1714319 A | 12/2005 |
| CN | 1756659 A | 4/2006 |
| CN | 1849187 A | 10/2006 |
| CN | 101746057 A | 6/2010 |
| CN | 102046129 A | 5/2011 |
| CN | 102300526 A | 12/2011 |
| CN | 103635167 A | 3/2014 |
| CN | 104470710 A | 3/2015 |
| CN | 105147456 A | 12/2015 |
| CN | 105829072 A | 8/2016 |
| CN | 105853067 A | 8/2016 |
| CN | 105997351 A | 10/2016 |
| CN | 106913422 A | 7/2017 |
| CN | 107072825 A | 8/2017 |
| CN | 107106362 A | 8/2017 |
| EP | 0989218 A1 | 3/2000 |
| EP | 1452157 A1 | 9/2004 |
| EP | 1473148 A1 | 11/2004 |
| EP | 1305248 B1 | 1/2006 |
| EP | 1393701 B1 | 7/2013 |
| EP | 3056176 A1 | 8/2016 |
| EP | 3092997 A1 | 11/2016 |
| EP | 3092997 B1 | 8/2017 |
| EP | 3251642 A1 | 12/2017 |

(56) References Cited

FOREIGN PATENT DOCUMENTS

| | | |
|---|---|---|
| EP | 3257488 A1 | 12/2017 |
| EP | 3563817 A1 | 11/2019 |
| JP | 56099175 A | 8/1981 |
| JP | 3213543 A | 9/1991 |
| JP | H03213543 A | 9/1991 |
| JP | H05501210 A | 3/1993 |
| JP | H06254117 A | 9/1994 |
| JP | 8071107 A | 3/1996 |
| JP | H08071107 A | 3/1996 |
| JP | H08132576 A | 5/1996 |
| JP | 2000026015 A | 1/2000 |
| JP | 2000160460 A | 6/2000 |
| JP | 3086141 B2 | 9/2000 |
| JP | 2001276120 A | 10/2001 |
| JP | 2002001855 A | 1/2002 |
| JP | 2002035029 A | 2/2002 |
| JP | 2002178428 A | 6/2002 |
| JP | 2002238934 A | 8/2002 |
| JP | 2002248127 A | 9/2002 |
| JP | 2003521949 A | 7/2003 |
| JP | 2004500169 A | 1/2004 |
| JP | 2004081365 A | 3/2004 |
| JP | 2004229857 A | 8/2004 |
| JP | 2004237410 A | 8/2004 |
| JP | 2004254862 A | 9/2004 |
| JP | 2004298362 A | 10/2004 |
| JP | 2005509096 A | 4/2005 |
| JP | 2005320636 A | 11/2005 |
| JP | 2006137147 A | 6/2006 |
| JP | 2006149747 A | 6/2006 |
| JP | 2006149749 A | 6/2006 |
| JP | 2006204673 A | 8/2006 |
| JP | 2007190397 A | 8/2007 |
| JP | H04030847 A | 1/2008 |
| JP | 2008029749 A | 2/2008 |
| JP | 2008055198 A | 3/2008 |
| JP | 2008104853 A | 5/2008 |
| JP | 2008105425 A | 5/2008 |
| JP | 2008148942 A | 7/2008 |
| JP | 2008154998 A | 7/2008 |
| JP | 2008179128 A | 8/2008 |
| JP | 2008194493 A | 8/2008 |
| JP | 2008229006 A | 10/2008 |
| JP | 2008229007 A | 10/2008 |
| JP | 2008253290 | 10/2008 |
| JP | 2008260131 A | 10/2008 |
| JP | 2008264480 A | 11/2008 |
| JP | 2008272250 A | 11/2008 |
| JP | 2008272253 A | 11/2008 |
| JP | 2008296585 A | 12/2008 |
| JP | 2009000161 A | 1/2009 |
| JP | 2009039341 A | 2/2009 |
| JP | 2009056156 A | 3/2009 |
| JP | 2009106667 A | 5/2009 |
| JP | 2009172231 A | 8/2009 |
| JP | 2009240804 A | 10/2009 |
| JP | 2009241607 A | 10/2009 |
| JP | 2010005918 A | 1/2010 |
| JP | 2013515871 A1 | 5/2010 |
| JP | 2010131833 A | 6/2010 |
| JP | 2011015707 A | 1/2011 |
| JP | 2011111165 A | 6/2011 |
| JP | 2011178124 A | 9/2011 |
| JP | 2011225000 A | 11/2011 |
| JP | 2012050882 A | 3/2012 |
| JP | 2012050883 A | 3/2012 |
| JP | 2012115358 A | 6/2012 |
| JP | 2012516203 A | 7/2012 |
| JP | 2012521498 A | 9/2012 |
| JP | 5124187 B2 | 11/2012 |
| JP | 5124188 B2 | 11/2012 |
| JP | 2013138795 A | 7/2013 |
| JP | 2014097257 A | 5/2014 |
| JP | 2014111222 A | 6/2014 |
| JP | 2014188042 A | 10/2014 |
| JP | 2015510831 A | 4/2015 |
| JP | 2015521499 A | 7/2015 |
| JP | 2015171501 A | 10/2015 |
| JP | 2016013687 A | 1/2016 |
| JP | 2016016536 A | 2/2016 |
| JP | 2016054989 A | 4/2016 |
| JP | 5942819 B2 | 6/2016 |
| JP | 2016193199 A | 11/2016 |
| JP | 6149635 B2 | 6/2017 |
| JP | 2019081304 A | 5/2019 |
| JP | 2019166804 A | 10/2019 |
| JP | 2019181807 A | 10/2019 |
| JP | 2020054741 A | 4/2020 |
| JP | 2020054742 A | 4/2020 |
| JP | 2020054744 A | 4/2020 |
| JP | 2020054745 A | 4/2020 |
| JP | 2022117131 A | 8/2022 |
| WO | 9207531 A1 | 5/1992 |
| WO | 9925296 A1 | 5/1999 |
| WO | 2003015681 | 2/2003 |
| WO | 2003059603 | 7/2003 |
| WO | 2008123348 A1 | 10/2008 |
| WO | 2011137962 A1 | 11/2011 |
| WO | 2013084977 A1 | 6/2013 |
| WO | 20140084168 | 6/2014 |
| WO | 2014196669 A2 | 12/2014 |
| WO | 2015165927 A1 | 11/2015 |
| WO | 2016047320 A1 | 3/2016 |
| WO | 2016063346 A1 | 4/2016 |
| WO | 2016067387 A1 | 5/2016 |
| WO | 2016071981 A1 | 5/2016 |
| WO | 2016075974 A1 | 5/2016 |
| WO | 2016098416 A1 | 6/2016 |
| WO | 2016104412 A1 | 6/2016 |
| WO | 2016104422 A1 | 6/2016 |
| WO | 20160056092 | 6/2016 |
| WO | 20160056093 | 6/2016 |
| WO | 2016158499 A1 | 10/2016 |
| WO | 2016158746 A1 | 10/2016 |
| WO | 2016208502 A1 | 12/2016 |
| WO | 2016208513 A1 | 12/2016 |
| WO | 2017105997 A1 | 6/2017 |
| WO | 2018061288 A1 | 4/2018 |
| WO | 2018084145 A1 | 5/2018 |
| WO | 2018154680 A1 | 8/2018 |
| WO | 2018154682 A1 | 8/2018 |
| WO | 2018167836 A1 | 9/2018 |
| WO | 2019046363 A1 | 3/2019 |
| WO | 2019111203 A1 | 6/2019 |
| WO | 2019150802 A1 | 8/2019 |
| WO | 2020006996 A1 | 1/2020 |

OTHER PUBLICATIONS

3D Nonwovens Developments for textured nonwovens; Sep. 19, 2017, pp. 1-2.
All Office Actions; U.S. Appl. No. 15/832,929, filed Dec. 6, 2017.
All Office Actions; U.S. Appl. No. 15/833,057, filed Dec. 6, 2017.
All Office Actions; U.S. Appl. No. 15/839,896, filed Dec. 13, 2017.
All Office Actions; U.S. Appl. No. 16/115,617, filed Aug. 29, 2018.
All Office Actions; U.S. Appl. No. 17/409,850, filed Aug. 24, 2021.
All Office Actions; U.S. Appl. No. 17/474,423, filed Sep. 14, 2021.
All Office Actions; U.S. Appl. No. 17/474,528, filed Sep. 14, 2021.
All Office Actions; U.S. Appl. No. 17/481,441, filed Sep. 22, 2021.
American Cancer Society—What Cancer Patients Their Families and Caregivers Need to Know About COVID 19—Is Impacting Our Patient Services, dated Mar. 31, 2020, pp. 1-3.
ASTM "Standard Tables of Body Measurements for Children Infant Size—Preemie to 24 Months", dated Mar. 30, 2020, pp. 1-6.
ASTM "Standard Tables of Body Measurements for Adult Females Misses Figure Type Size Range 00-20" dated May 12, pp. 1-7.
All Office Actions; U.S. Appl. No. 18/298,437, filed Apr. 11, 2023.
All Office Actions; U.S. Appl. No. 18/298,453, filed Apr. 11, 2023.
Unpublished U.S. Appl. No. 18/298,437, filed Apr. 11, 2023 to Uwe Schneider et al.

(56) References Cited

OTHER PUBLICATIONS

Unpublished U.S. Appl. No. 18/298,453, filed Apr. 11, 2023 to Uwe Schneider et al.

* cited by examiner

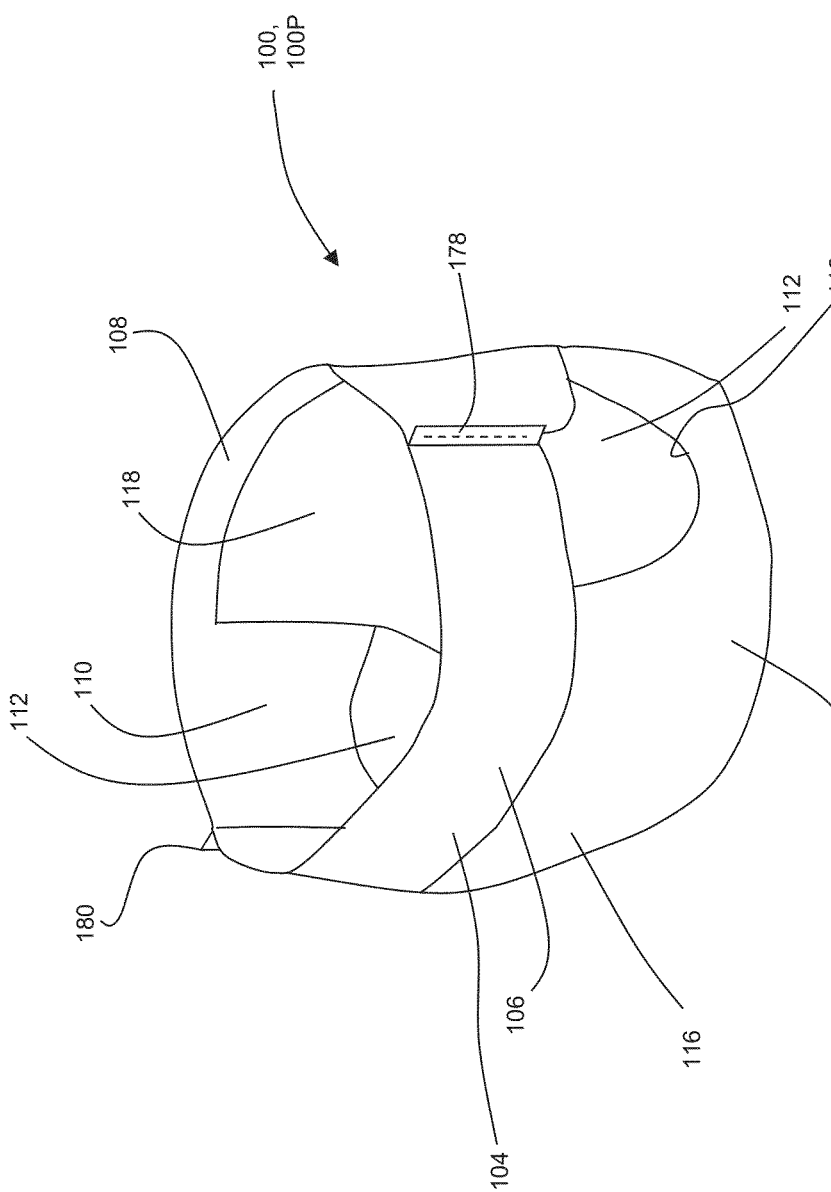

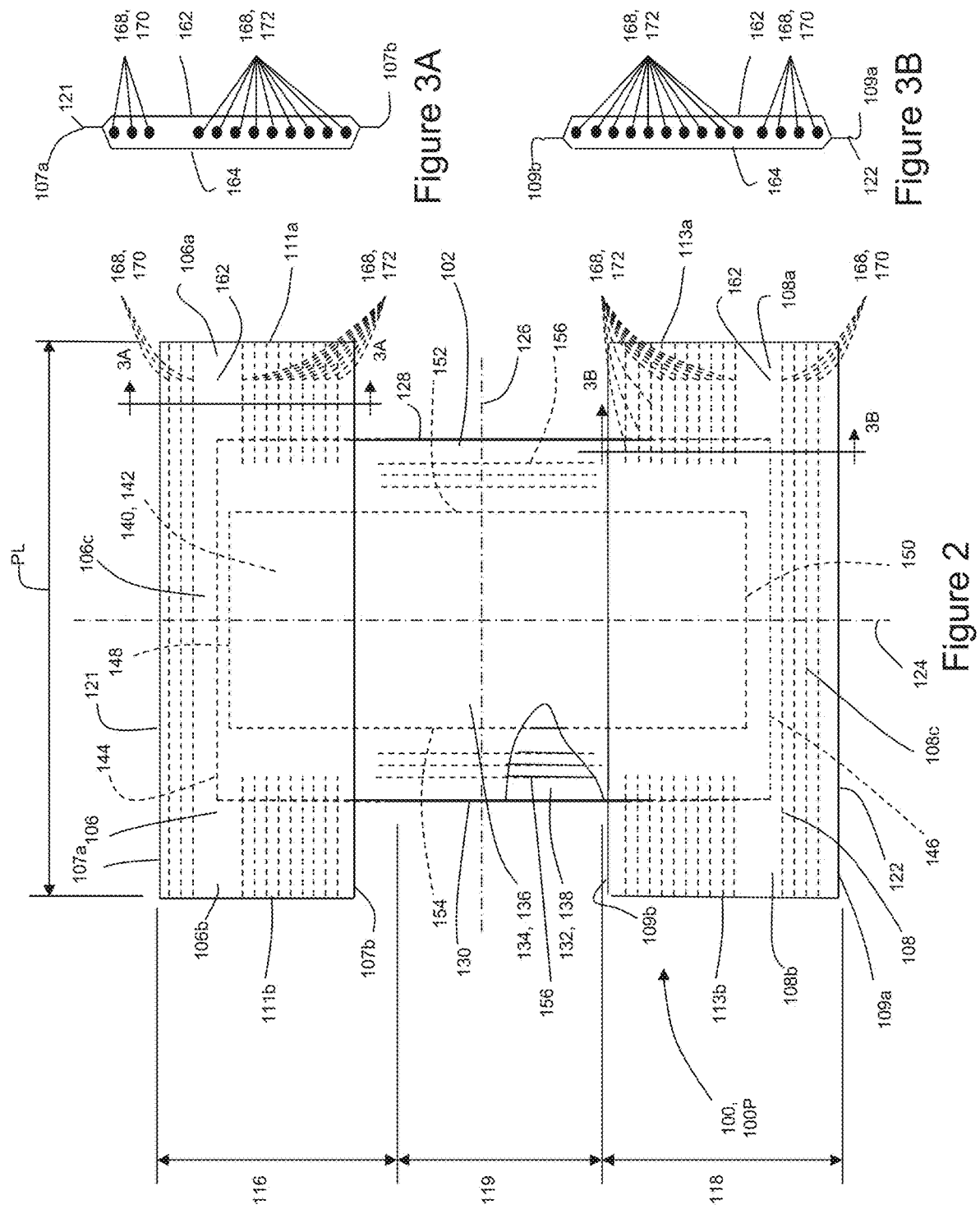

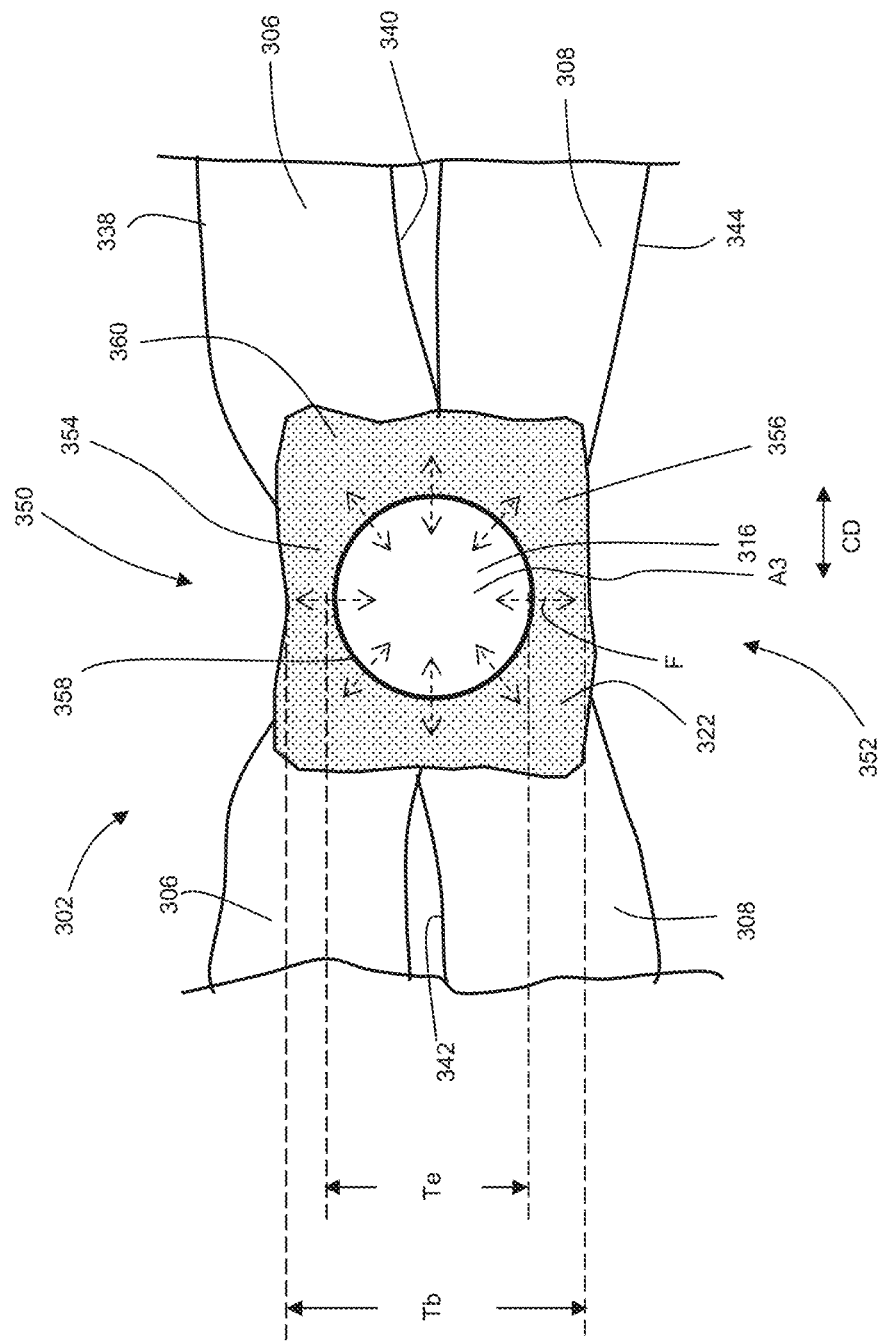

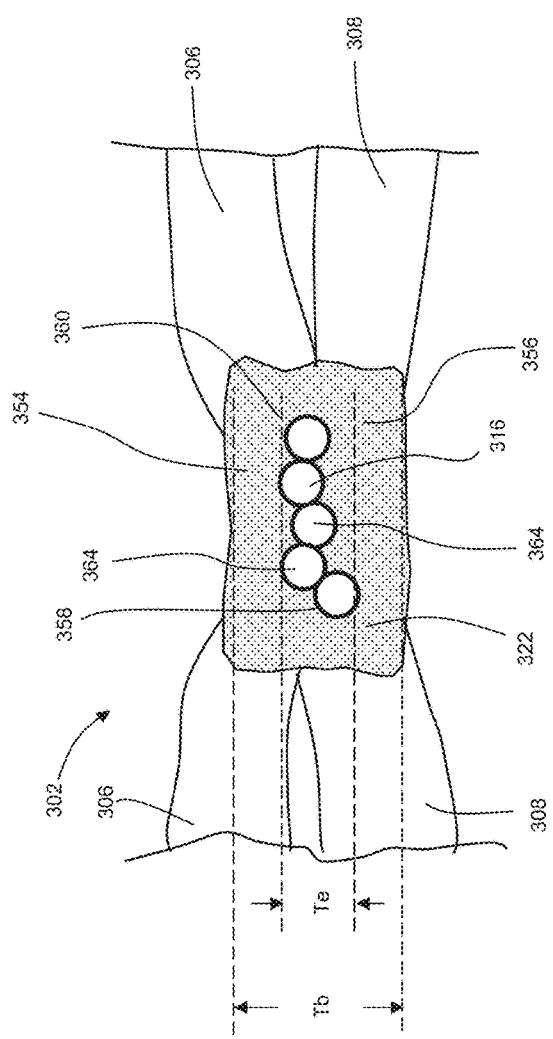
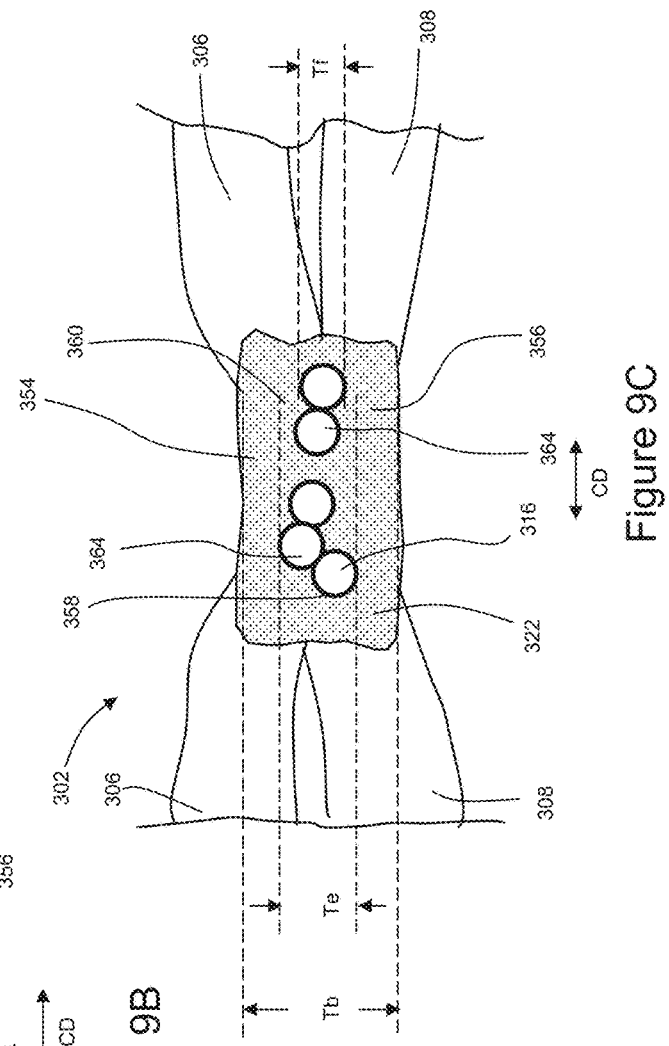

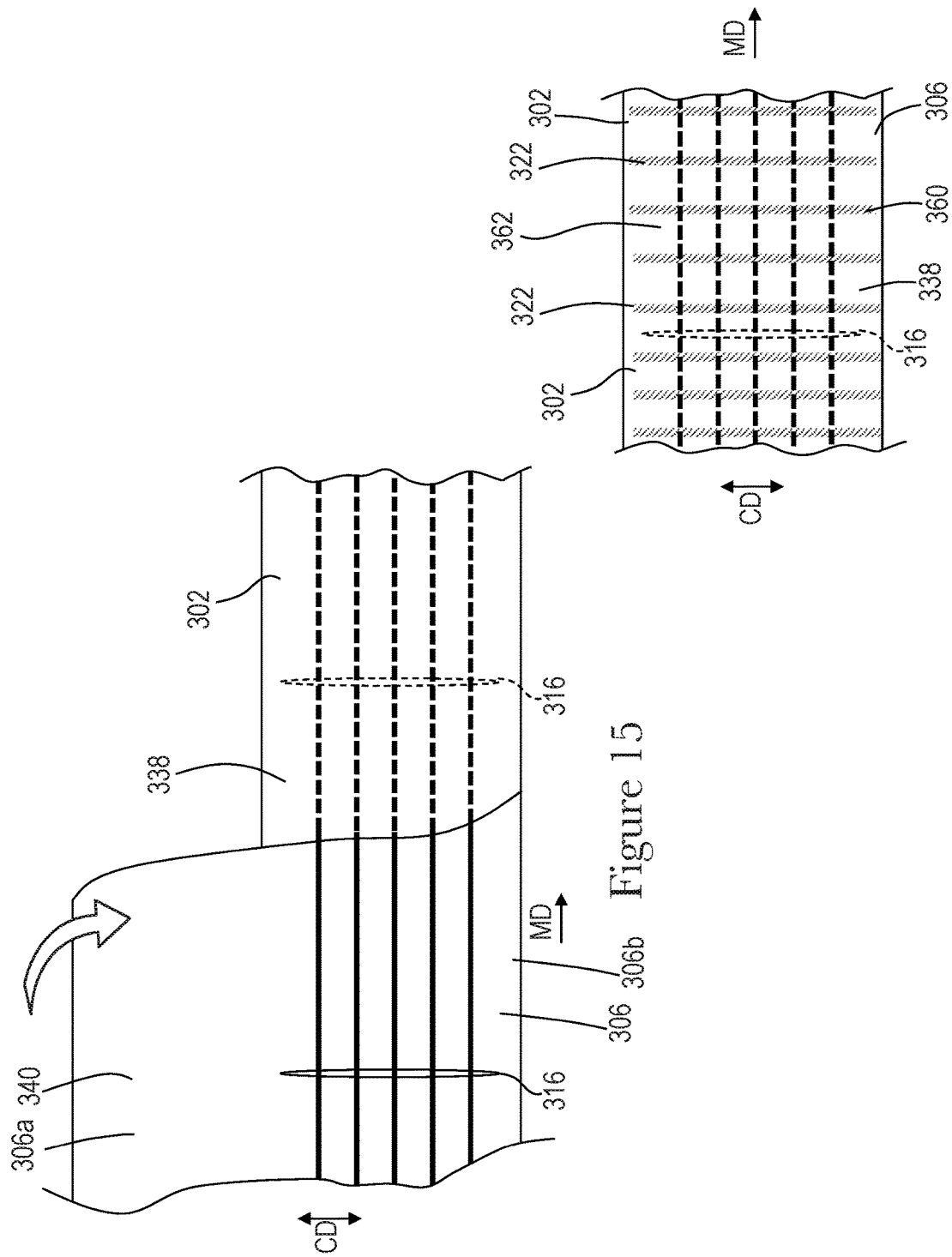

METHODS AND APPARATUSES FOR MAKING ELASTOMERIC LAMINATES

CROSS REFERENCE TO RELATED APPLICATIONS

This application is a continuation of U.S. application Ser. No. 17/409,850, filed on Aug. 24, 2021, which is a continuation of U.S. patent application Ser. No. 16/115,617, filed on Aug. 29, 2018, which claims the benefit, under 35 USC 119(e), to U.S. Provisional Patent Application No. 62/686,896, filed on Jun. 19, 2108 (P&G 15273P); U.S. Provisional Patent Application No. 62/687,031, filed on Jun. 19, 2018 (P&G 15271P); U.S. Provisional Patent Application No. 62/685,429, filed on Jun. 15, 2018 (P&G 15275P); U.S. Provisional Patent Application No. 62/581,278, filed on Nov. 3, 2017 (P&G 15007P); U.S. Provisional Patent Application No. 62/553,149, filed on Sep. 1, 2017 (P&G 14917P); U.S. Provisional Patent Application No. 62/553,538, filed on Sep. 1, 2017 (P&G 14921P); and U.S. Provisional Patent Application No. 62/553,171, filed on Sep. 1, 2017 (P&G 14918P); each of which are herein incorporated by reference in their entirety.

FIELD OF THE INVENTION

The present disclosure relates to methods for manufacturing absorbent articles, and more particularly, to apparatuses and methods for making elastomeric laminates that may be used as components of absorbent articles.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from an advancing web or webs are combined with other individual components created from other advancing webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

Some absorbent articles have components that include elastomeric laminates. Such elastomeric laminates may include an elastic material bonded to one or more nonwovens. The elastic material may include an elastic film and/or elastic strands. In some laminates, a plurality of elastic strands are joined to a nonwoven while the plurality of strands are in a stretched condition so that when the elastic strands relax, the nonwoven gathers between the locations where the nonwoven is bonded to the elastic strands, and in turn, forms corrugations. The resulting elastomeric laminate is stretchable to the extent that the corrugations allow the elastic strands to elongate.

In some assembly processes, stretched elastic strands may be advanced in a machine direction and may be adhered between two advancing substrates, wherein the stretched elastic strands are spaced apart from each other in a cross direction. Some assembly processes are also configured with several elastic strands that are very closely spaced apart from each other in the cross direction. In some configurations, close cross directional spacing between elastic strands can be achieved by drawing elastic strands from windings that have been stacked in the cross direction on a beam. For example, various textile manufacturers may utilize beam elastics and associated handling equipment, such as available from Karl Mayer Corporation.

However, problems can be encountered in manufacturing processes when drawing elastic strands stacked on a beam. For example, relatively low decitex elastic strands supplied on a beam may include a coating, sometimes referred to a yarn finish or spin finish, to help prevent the elastics strands from adhering to themselves, each other, and/or downstream handling equipment. When constructing absorbent articles, hot melt adhesives are sometimes used to adhere stretched elastic stands to advancing substrates to create elastic laminates. However, hot melt adhesives used to adhere stretched elastic strands to substrates when constructing absorbent articles may not adhere well to strands having a spin finish. As such, increased amounts of adhesive may be required to adequately adhere the stretched elastic strands to the substrates than would otherwise be required for elastic stands without a spin finish. In turn, relatively larger amounts of adhesives required to bond the elastic strands to the substrates may have a negative impact on aspects of the resulting product, such as with respect to costs, functionality, and aesthetics.

In an attempt to overcome the aforementioned problems associated with adhesives, some assembly processes may be configured to apply mechanical bonds with heat and pressure to trap the stretched elastic strands between two substrates. Such mechanical bonds may be created, for example, by advancing the substrates and elastic strands between an ultrasonic horn and anvil. However, the heat and pressure from the anvil and horn may also sever the elastic strands. In some instances, the runout of the anvil can cause variations in the distance between the ultrasonic horn and anvil during the bonding process. Such distance variations can cause the elastic strands to be severed during the bonding process and/or result in relatively inconsistent bond quality. It may be possible to mitigate problems associated with severing the elastic strands by operating at relatively slow speeds. For example, at relatively slow advancement speeds, relatively less pressure may be exerted on the elastic strands during the bonding process. In addition, the ultrasonic horn may be configured to move toward and away from the anvil during the bonding process in order to compensate for relatively large runout values on the anvil. However, disposable absorbent article manufacturing lines may operate at relatively high speeds. As such, it can be inefficient and/or cost prohibitive to reduce the advancement speeds in high speed manufacturing operations to achieve the desired bond qualities without severing the elastic strands. In addition, ultrasonic horns may not be able to compensate for relatively high anvil runout values at high speeds. In some configurations, grooves may be provided in the horn or anvil for the elastic strands to nest in and to shield the elastic strands from pressure and prevent severing through the bonding process, such as disclosed in U.S. Pat. No. 6,291,039 and European Patent Publication No. EP 3 092 997 B1. However, positioning hundreds of elastic strands drawn from a beam in nesting grooves on an ultrasonic horn and/or anvil may add complexity to the assembly process.

Consequently, it would be beneficial to provide methods and apparatuses for producing elastomeric laminates at relatively high advancement speeds by mechanically bonding elastic strands between substrates without severing the elastics strands, and/or without the need for having to guide elastic strands into designated nesting grooves in a mechanical bonding device.

SUMMARY OF THE INVENTION

In one aspect, a method for making absorbent articles comprises steps of: rotating a pattern roll about an axis of rotation extending axially in a cross direction, the pattern roll comprising bonding surfaces extending radially outward from the axis of rotation; providing a pressing surface adjacent the pattern roll to define a nip between the pattern roll and the pressing surface; advancing a first substrate and a second substrate through in a machine direction through the nip at a first speed S1 of at least about 100 meters per minute; providing elastic strands wound onto a beam; rotating the beam to unwind the elastic strands from the beam; advancing the elastic strands from the rotating beam; stretching the elastic strands; and bonding the stretched elastic strands between the first substrate and the second substrate at the nip to form an elastomeric laminate.

In another aspect, a method for making absorbent articles comprises steps of: rotating a pattern roll about an axis of rotation extending axially in a cross direction, the pattern roll comprising bonding surfaces extending radially outward from the axis of rotation; providing an ultrasonic horn comprising an energy transfer surface to define a nip between the pattern roll and the energy transfer surface; advancing a first substrate and a second substrate through in a machine direction through the nip at a first speed S1 of at least about 100 meters per minute; providing elastic strands wound onto a beam; rotating the beam to unwind the elastic strands from the beam; advancing the elastic strands from the rotating beam; stretching the elastic strands; and bonding the stretched elastic strands between the first substrate and the second substrate at the nip to form an elastomeric laminate.

In yet another aspect, a method for making absorbent articles comprises steps of: rotating a pattern roll about an axis of rotation extending axially in a cross direction, the pattern roll comprising bonding surfaces extending radially outward from the axis of rotation; providing an ultrasonic horn comprising an energy transfer surface to define a nip between the pattern roll and the energy transfer surface; advancing a first substrate and a second substrate through in a machine direction through the nip at a first speed S1 of at least about 100 meters per minute; providing elastic strands wound onto a beam; rotating the beam to unwind the elastic strands from the beam; advancing the elastic strands from the rotating beam; stretching the elastic strands; positioning the stretched elastic strands between the first substrate and the second substrate; and welding the first substrate and the second substrate together at the nip to form an elastomeric laminate.

BRIEF DESCRIPTION OF THE DRAWINGS

FIG. 1A is a front perspective view of a diaper pant.
FIG. 2 is a partially cut away plan view of the diaper pant shown in FIGS. 1A and 1B in a flat, uncontracted state.

FIG. 3A is a cross-sectional view of the diaper pant of FIG. 2 taken along line 3A-3A.
FIG. 3B is a cross-sectional view of the diaper pant of FIG. 2 taken along line 3B-3B.
FIG. 8C is a sectional view of the elastic strand in a bonded region of FIG. 7D taken along line 8C-8C, wherein the elastic strand is in a relaxed state.
FIG. 9B is a sectional view of an elastic strand, bond, first substrate, and second substrate of FIG. 7A taken along line 8A-8A, wherein a plurality of filaments of the elastic strand are bonded in a second configuration.
FIG. 9C is a sectional view of an elastic strand, bond, first substrate, and second substrate of FIG. 7A taken along line 8A-8A, wherein a plurality of filaments of the elastic strand are bonded in a third configuration.

FIG. 15 is a view of the converting apparatus of FIG. 14 taken along line 15-15.

FIG. 16 is a view of the converting apparatus of FIG. 14 taken along line 16-16.

DETAILED DESCRIPTION OF THE INVENTION

Figure 1B:
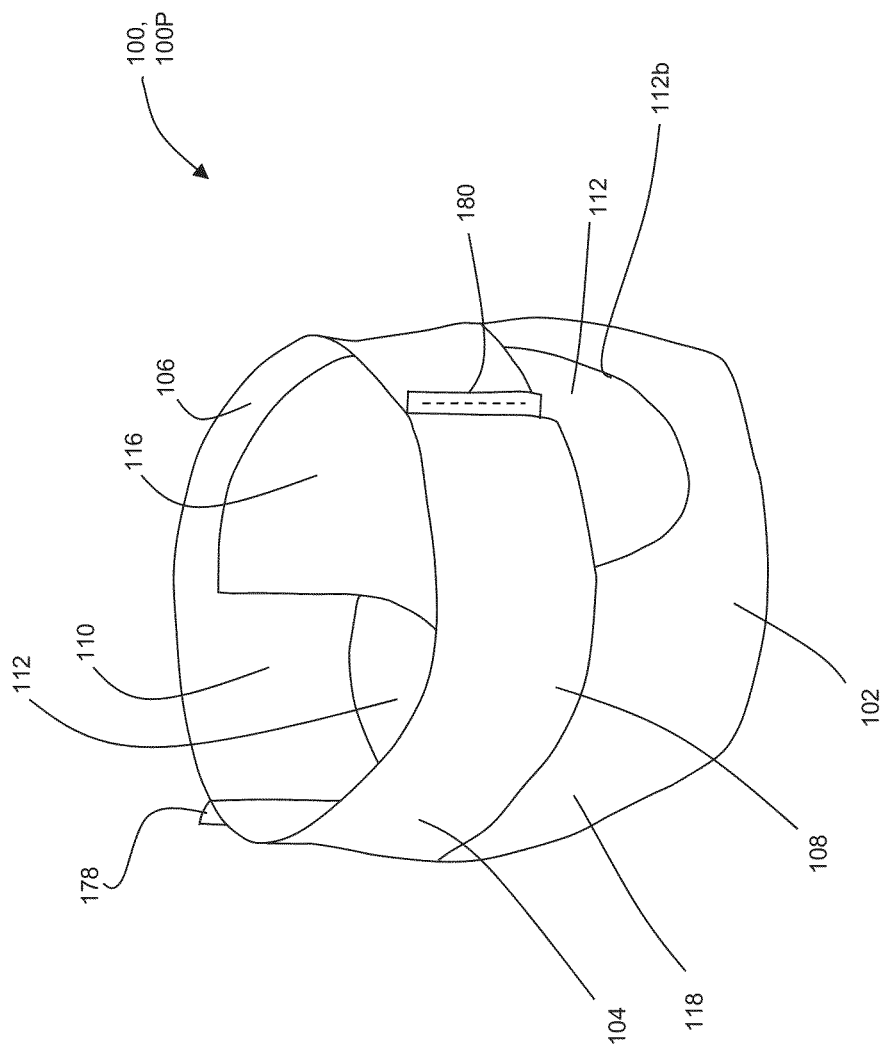
FIG. 1B is a rear perspective view of a diaper pant.

The following term explanations may be useful in understanding the present disclosure:

"Absorbent article" is used herein to refer to consumer products whose primary function is to absorb and retain soils and wastes. Absorbent articles can comprise sanitary napkins, tampons, panty liners, interlabial devices, wound dressings, wipes, disposable diapers including taped diapers and diaper pants, inserts for diapers with a reusable outer cover, adult incontinent diapers, adult incontinent pads, and adult incontinent pants. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674, 216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1, all of which are incorporated by reference herein.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 4,940,464; 5,092,861; 5,246,433; 5,569,234; 5,897, 545; 5,957,908; 6,120,487; 6,120,489; 7,569,039 and U.S. Patent Publication Nos. 2003/0233082 A1; 2005/0107764 A1, 2012/0061016 A1, 2012/0061015 A1; 2013/0255861 A1; 2013/0255862 A1; 2013/0255863 A1; 2013/0255864 A1; and 2013/0255865 A1, all of which are incorporated by reference herein.

The present disclosure relates to methods for manufacturing absorbent articles, and in particular, to methods for making elastomeric laminates that may be used as components of absorbent articles. The elastomeric laminates may include a first substrate, a second substrate, and an elastic material positioned between the first substrate and second substrate. During the process of making the elastomeric laminate, the elastic material may be advanced and stretched in a machine direction and may be joined with either or both the first and second substrates advancing in the machine direction. The methods and apparatuses according to the present disclosure may be configured with a plurality of elastic strands wound onto a beam, and wherein one or more elastic strands may comprise a spin finish. During assembly of an elastomeric laminate, the beam is rotated to unwind the elastic strands from the beam. The elastic strands may also be stretched while advancing in a machine direction. Discrete mechanical bonds are applied to the first substrate and the second substrate to secure elastic strands therebetween, wherein the discrete bonds are arranged intermittently along the machine direction. As discussed in more detail below, when combining elastic strands having relatively low decitex values with substrates to create bonds having certain ranges of thicknesses, the mechanical bonds can be applied to secure the elastic strands between substrates without severing the elastics strands and without the need for nesting grooves in a mechanical bonding device. The bonding process can be achieved at relatively high substrate advancement speeds when utilizing mechanical bonding devices that require none or relatively small online adjustments, such as for example, patterned and anvil rolls and/or ultrasonic bonding devices with relatively low runout values.

During the bonding process, heat and pressure are applied to the first substrate and the second substrate such that malleable materials of the first and second substrates deform to completely surround an outer perimeter of a discrete length of the stretched elastic strand. After removing the heat and pressure from the first and second substrates, the malleable materials harden to define a bond conforming with a cross sectional shape defined by the outer perimeter of the stretched elastic strand. When the elastic strand is in a stretched state, the stretched elastic strand defines a cross sectional area that is less than a cross sectional area of the elastic strand when in a relaxed state. Thus, when tension is released from the elastic strand, the cross sectional area of the elastic strand is prevented from expanding in the bond by the hardened materials of the first and second substrates, which in turn, creates forces between the elastic strand and the hardened materials. The forces between the elastic strand and the hardened materials increases the friction between the elastic strand and the hardened materials. Thus, a frictional lock may be created between the elastic strand and the hardened materials in the bond region by releasing the tension from the stretched elastic strands. The frictional lock holds the discrete length of the elastic strand in a fixed position in the bond region with the first and second substrates.

To help provide additional context to the subsequent discussion of the process embodiments, the following provides a general description of absorbent articles in the form of diapers that include components including the elastomeric laminates that may be produced with the methods and apparatuses disclosed herein.

FIGS. 1A, 1B, and 2 show an example of an absorbent article 100 in the form of a diaper pant 100P that may include components constructed from elastomeric laminates assembled in accordance with the apparatuses and methods disclosed herein. In particular, FIGS. 1A and 1B show perspective views of a diaper pant 100P in a pre-fastened configuration, and FIG. 2 shows a plan view of the diaper pant 100P with the portion of the diaper that faces away from a wearer oriented toward the viewer. The diaper pant 100P includes a chassis 102 and a ring-like elastic belt 104. As discussed below in more detail, a first elastic belt 106 and a second elastic belt 108 are bonded together to form the ring-like elastic belt 104.

With continued reference to FIG. 2, the diaper pant 100P and the chassis 102 each include a first waist region 116, a second waist region 118, and a crotch region 119 disposed intermediate the first and second waist regions. The first waist region 116 may be configured as a front waist region, and the second waist region 118 may be configured as back waist region. The diaper 100P may also include a laterally extending front waist edge 121 in the front waist region 116 and a longitudinally opposing and laterally extending back waist edge 122 in the back waist region 118. To provide a frame of reference for the present discussion, the diaper 100P and chassis 102 of FIG. 2 are shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1A, 1B, and 2, the diaper pant 100P may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100P may also include other features, such as leg elastics and/or leg cuffs to enhance the fit around the legs of the wearer.

As shown in FIG. 2, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2, the laterally extending end edges 144 and 146 are located longitudinally inward from the laterally extending front waist edge 121 in the front waist region 116 and the laterally extending back waist edge 122 in the back waist region 118. When the diaper pant 100P is worn on the lower torso of a wearer, the front waist edge 121 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

As previously mentioned, the diaper pant 100P may include a backsheet 136. The backsheet 136 may also define the outer surface 134 of the chassis 102. The backsheet 136 may also comprise a woven or nonwoven material, polymeric films such as thermoplastic films of polyethylene or polypropylene, and/or a multi-layer or composite materials comprising a film and a nonwoven material. The backsheet may also comprise an elastomeric film. An example backsheet 136 may be a polyethylene film having a thickness of from about 0.012 mm (0.5 mils) to about 0.051 mm (2.0 mils). Further, the backsheet 136 may permit vapors to escape from the absorbent core (i.e., the backsheet is breathable) while still preventing exudates from passing through the backsheet 136.

Also described above, the diaper pant 100P may include a topsheet 138. The topsheet 138 may also define all or part of the inner surface 132 of the chassis 102. The topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams;

reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art. Topsheets 138 may be selected from high loft nonwoven topsheets, apertured film topsheets and apertured nonwoven topsheets. Exemplary apertured films may include those described in U.S. Pat. Nos. 5,628,097; 5,916,661; 6,545,197; and 6,107,539.

As mentioned above, the diaper pant 100P may also include an absorbent assembly 140 that is joined to the chassis 102. As shown in FIG. 2, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 A1 and 2004/0097895 A1.

As previously mentioned, the diaper 100P may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; and U.S. Patent Publication No. 2009/0312730 A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIGS. 1A and 1B. The ring-like elastic belt may be formed by joining a first elastic belt to a second elastic belt with a permanent side seam or with an openable and reclosable fastening system disposed at or adjacent the laterally opposing sides of the belts.

As previously mentioned, the ring-like elastic belt 104 may be defined by a first elastic belt 106 connected with a second elastic belt 108. As shown in FIG. 2, the first elastic belt 106 extends between a first longitudinal side edge 111a and a second longitudinal side edge 111b and defines first and second opposing end regions 106a, 106b and a central region 106c. And the second elastic 108 belt extends between a first longitudinal side edge 113a and a second longitudinal side edge 113b and defines first and second opposing end regions 108a, 108b and a central region 108c. The distance between the first longitudinal side edge 111a and the second longitudinal side edge 111b defines the pitch length, PL, of the first elastic belt 106, and the distance between the first longitudinal side edge 113a and the second longitudinal side edge 113b defines the pitch length, PL, of the second elastic belt 108. The central region 106c of the first elastic belt is connected with the first waist region 116 of the chassis 102, and the central region 108c of the second elastic belt 108 is connected with the second waist region 118 of the chassis 102. As shown in FIGS. 1A and 1B, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2, 3A, and 3B, the first elastic belt 106 also defines an outer laterally extending edge 107a and an inner laterally extending edge 107b, and the second elastic belt 108 defines an outer laterally extending edge 109a and an inner laterally extending edge 109b. As such, a perimeter edge 112a of one leg opening may be defined by portions of the inner laterally extending edge 107b of the first elastic belt 106, the inner laterally extending edge 109b of the second elastic belt 108, and the first longitudinal or right side edge 128 of the chassis 102. And a perimeter edge 112b of the other leg opening may be defined by portions of the inner laterally extending edge 107b, the inner laterally extending edge 109b, and the second longitudinal or left side edge 130 of the chassis 102. The outer laterally extending edges 107a, 109a may also define the front waist edge 121 and the laterally extending back waist edge 122 of the diaper pant 100P. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer substrate layer 162 and the inner substrate layer 164. The belt elastic material may include one or more elastic elements such as strands, ribbons, films, or panels extending along the lengths of the elastic belts. As shown in FIGS. 2, 3A, and 3B, the belt elastic material may include a plurality of elastic strands 168 which may be referred to herein as outer, waist elastics 170 and inner, waist elastics 172. Elastic strands 168, such as the outer waist elastics 170, may continuously extend laterally between the first and second opposing end regions 106a, 106b of the first elastic belt 106 and between the first and second opposing end regions 108a, 108b of the second elastic belt 108. In some embodiments, some elastic strands 168, such as the inner waist elastics 172, may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2. The belt elastic material may be joined to the outer and/or inner layers continuously or intermittently along the interface between the belt elastic material and the inner and/or outer belt layers.

In some configurations, the first elastic belt 106 and/or second elastic belt 108 may define curved contours. For example, the inner lateral edges 107b, 109b of the first and/or second elastic belts 106, 108 may include non-linear or curved portions in the first and second opposing end regions. Such curved contours may help define desired shapes to leg opening 112, such as for example, relatively rounded leg openings. In addition to having curved contours, the elastic belts 106, 108 may include elastic strands 168, 172 that extend along non-linear or curved paths that may correspond with the curved contours of the inner lateral edges 107b, 109b.

It is to be appreciated that the apparatuses and methods of assembly of elastomeric laminates and absorbent articles described herein and illustrated in the accompanying drawings are non-limiting example configurations. The features illustrated or described in connection with one non-limiting configuration may be combined with the features of other non-limiting configurations. Such modifications and variations are intended to be included within the scope of the present disclosure.

As previously mentioned, apparatuses and methods according to the present disclosure may be utilized to produce elastomeric laminates that may be used to construct various components of diapers, such as elastic belts, leg cuffs, and the like. For example, FIGS. 4-17 show schematic views of converting apparatuses 300 adapted to manufacture elastomeric laminates 302. As described in more detail below, the converting apparatuses 300 shown in FIGS. 4-17 operate to advance a continuous length of elastic material 304, a continuous length of a first substrate 306, and a continuous length of a second substrate 308 along a machine direction MD. It is also to be appreciated that in some configurations, the first substrate 306 and second substrate 308 herein may be defined by two discrete substrates or may be defined by folded portions of a single substrate. The apparatus 300 stretches the elastic material 304 and joins the stretched elastic material 304 with the first and second substrates 306, 308 to produce an elastomeric laminate 302. Although the elastic material 304 is illustrated and referred to herein as strands, it is to be appreciated that elastic material 304 may include one or more continuous lengths of elastic strands, ribbons, and/or films.

It is to be appreciated that the elastomeric laminates 302 can be used to construct various types of absorbent article components. It also to be appreciated that the methods and apparatuses herein may be adapted to operate with various types of absorbent article assembly processes, such as disclosed for example in U.S. Patent Publication Nos. 2013/0255861 A1; 2013/0255862 A1; 2013/0255863 A1; 2013/0255864 A1; and 2013/0255865 A1. For example, the elastomeric laminates 302 may be used as a continuous length of elastomeric belt material that may be converted into the first and second elastic belts 106, 108 discussed above with reference to FIGS. 1-3B. As such, the elastic material 304 may correspond with the belt elastic material 168 interposed between the outer layer 162 and the inner layer 164, which in turn, may correspond with either the first and/or second substrates 306, 308. In other examples, the elastomeric laminates may be used to construct waistbands and/or side panels in taped diaper configurations. In yet other examples, the elastomeric laminates may be used to construct various types of leg cuff and/or topsheet configurations.

As discussed in more detail below, the converting apparatuses 300 may include metering devices arranged along a process machine direction MD, wherein the metering devices may be configured to stretch the advancing elastic material and/or join stretch elastic material with one or more advancing substrates. In some configurations, a metering device may comprise a beam of elastic strands wound thereon. During operation, elastic material may advance in a machine direction from a rotating beam to a downstream metering device to be joined with one or more advancing substrates. Bonds are applied to the first substrate and the second substrate to secure discrete lengths of the stretched elastic strands between the first and second substrates. The discrete bonds may be arranged intermittently along the machine direction. In some configurations, the bonds extend in the machine direction and may extend in a cross direction across one or more elastic strands. In some configurations, bonds may be separated from each other in a cross direction. It is to be appreciated that the apparatuses and methods of assembly of elastomeric laminates and absorbent articles described herein and illustrated in the accompanying drawings are non-limiting example configurations. The features illustrated or described in connection with one non-limiting configuration may be combined with the features of other non-limiting configurations. Such modifications and variations are intended to be included within the scope of the present disclosure.

Figure 4:
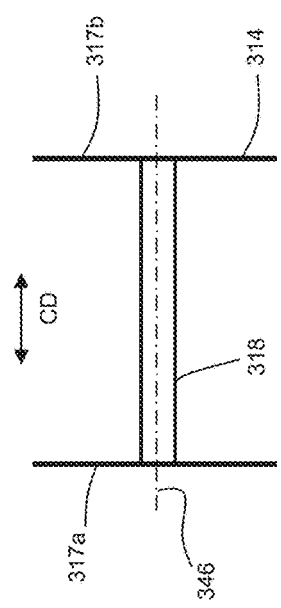
FIG. 4 shows an example of an empty beam having two side plates connected with opposing end portions of a mandrel core.
Figure 6:
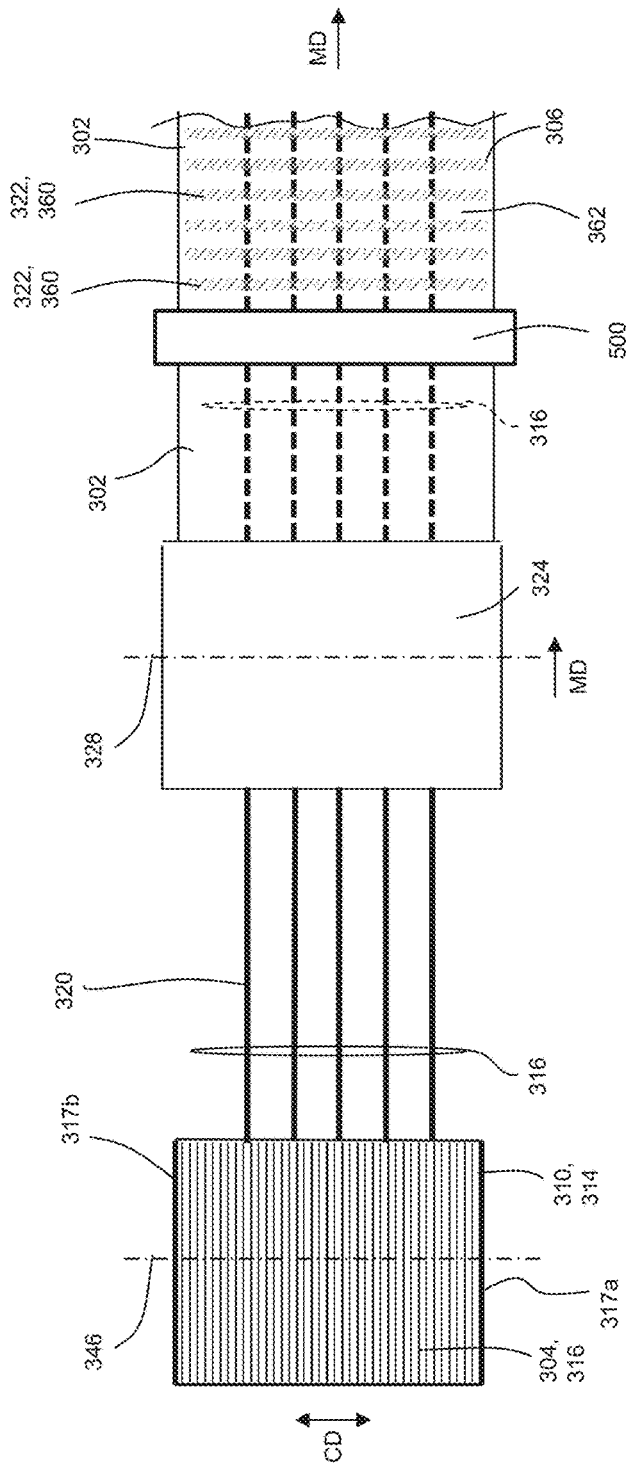
FIG. 6 is a view of the converting apparatus of FIG. 5 taken along line 6-6.
Figure 5:
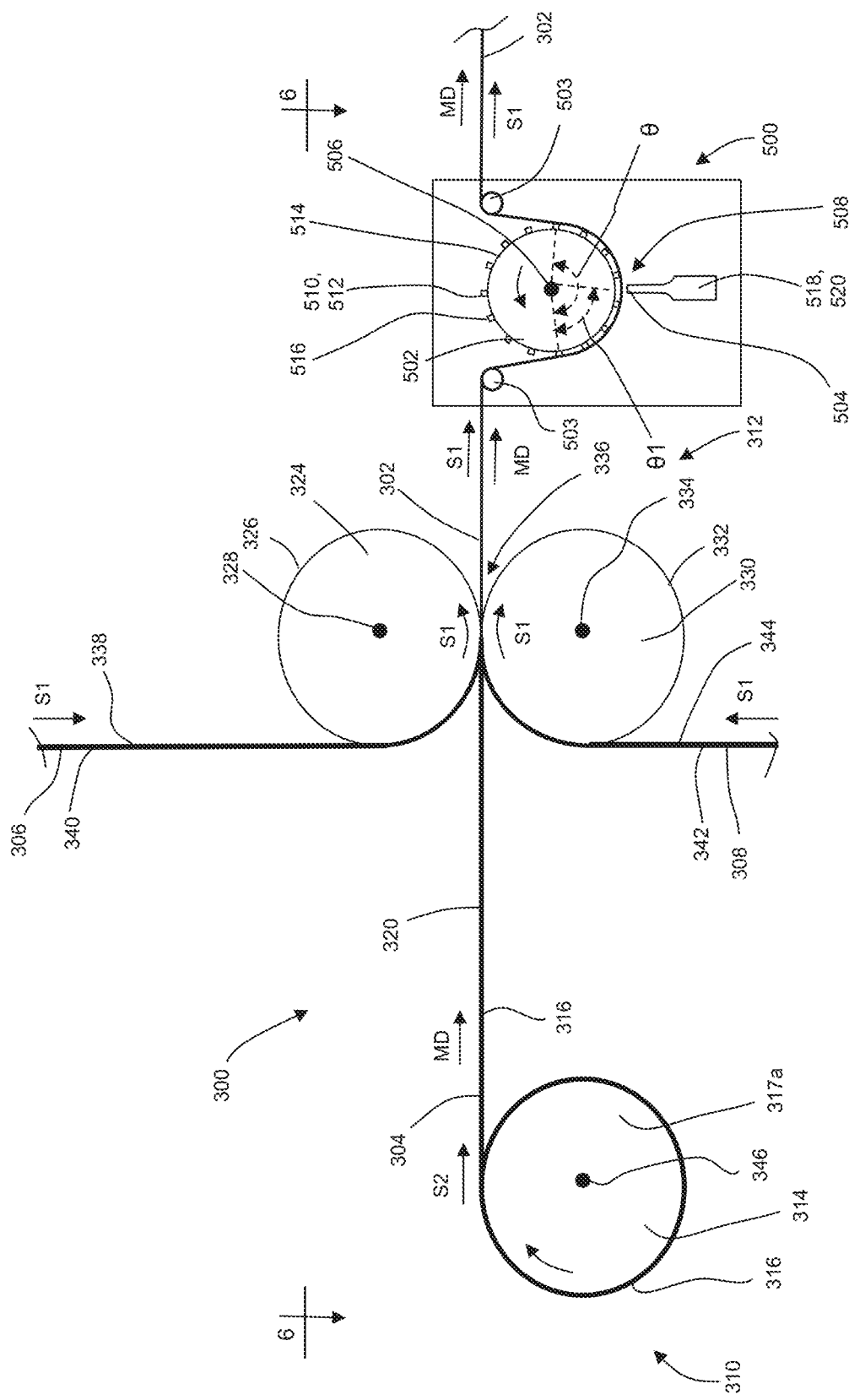
FIG. 5 is a schematic side view of a converting apparatus joining stretched elastic strands between a first substrate and a second substrate.

As shown in FIGS. 5 and 6, a converting apparatus 300 for producing an elastomeric laminate 302 may include a first metering device 310 and a second metering device 312. The first metering device 310 may be configured as a beam 314 with a plurality of elastic strands 316 wound thereon. FIG. 4 shows an example of an empty beam 314 that includes two side plates 317a, 317b that may be connected with opposing end portions of a mandrel core 318, wherein elastic strands may be wound onto the mandrel core 318. It is to be appreciated that beams of various sizes and technical specifications may be utilized in accordance with the methods and apparatuses herein, such as for example, beams that are available from ALUCOLOR Textilmaschinen, GmbH. During operation, the plurality of elastic strands 316 advance in the machine direction MD from the beam 314 to the second metering device 312. In addition, the plurality of elastic strands 316 may be stretched along the machine direction MD between the beam 314 and the second metering device 312. The stretched elastic strands 316 are also joined with a first substrate 306 and a second substrate 308 at the second metering device 312 to produce an elastomeric laminate 302. In some configurations, one or more of the elastic strands 316 advancing from the beam 314 may also include a spin finish 320 located on outer surfaces of the elastics strands. In turn, stretched elastic strands 316 may be connected between the first substrate 306 and the second substrate 308 with bonds 322. The bonds 322 may be configured as discrete mechanical bonds 322 applied to the first substrate 306 and the second substrate 308 to secure the elastic strands 316. The discrete bonds 322 may be arranged intermittently along the machine direction. In some configurations, the bonds 322 extend in the machine direction MD and may extend in the cross direction CD across one or more elastic strands 316. In some configurations, discrete bonds 322 may also be separated from each other in the cross direction CD.

As shown in FIGS. 5 and 6, the second metering device 312 may include: a first roller 324 having an outer circumferential surface 326 and that rotates about a first axis of rotation 328, and a second roller 330 having an outer circumferential surface 332 and that rotates about a second axis of rotation 334. The first roller 324 and the second roller 330 rotate in opposite directions, and the first roller 324 is adjacent the second roller 330 to define a nip 336 between the first roller 324 and the second roller 330. The first roller 324 rotates such that the outer circumferential surface 326 has a surface speed S1, and the second roller 330 may rotate such that the outer circumferential surface 332 has the same, or substantially the same, surface speed S1.

With continued reference to FIGS. 5 and 6, the first substrate 306 includes a first surface 338 and an opposing second surface 340, and the first substrate 306 advances to the first roller 324. In particular, the first substrate 306 advances at speed S1 to the first roller 324 where the first substrate 306 partially wraps around the outer circumferential surface 326 of the first roller 324 and advances through the nip 336. As such, the first surface 338 of the first substrate 306 travels in the same direction as and in contact with the outer circumferential surface 326 of the first roller 324. In addition, the second substrate 308 includes a first surface 342 and an opposing second surface 344, and the second substrate 308 advances to the second roller 330. In particular, the second substrate 308 advances at speed S1 to the second roller 330 where the second substrate 308 partially wraps around the outer circumferential surface 332 of the second roller 330 and advances through the nip 336. As such, the second surface 344 of the second substrate 308 travels in the same direction as and in contact with the outer circumferential surface 332 of the second roller 330.

Still referring to FIGS. 5 and 6, the beam 314 includes elastic strands 316 wound thereon, and the beam 314 is rotatable about a beam rotation axis 346. In some configurations, the beam rotation axis 346 may extend in the cross direction CD. As the beam 314 rotates, the elastic strands 316 advance from the beam 314 at a speed S2 with the elastic strands 316 being spaced apart from each other in the cross direction CD. From the beam 314, the elastic strands 316 advance in the machine direction MD to the nip 336. In some configurations, the speed S2 is less than the speed S1, and as such, the elastic strands 316 are stretched in the machine direction MD. In turn, the stretched elastic strands 316 advance through the nip 336 between the first and second substrates 306, 308 such that the elastic strands 316 are joined with the second surface 340 of the first substrate 306 and the first surface 342 of the second substrate 308 to produce a continuous length of elastomeric laminate 302.

It is to be appreciated that the beam 314 may be configured in various ways and with various quantities of elastic strands. Example beams, also referred to as warp beams, that may be used with the apparatus and methods herein are disclosed in U.S. Pat. Nos. 4,525,905; 5,060,881; and 5,775,380; and U.S. Patent Publication No. 2004/0219854 A1. Although FIG. 6 shows five elastic strands 316 advancing from the beam 314, it is to be appreciated that the apparatuses herein may be configured such that more or less than five elastic strands 316 advance from the beam 314. In some configurations, the elastic strands 316 advancing from the beam 314 may include from about 100 to about 2000 strands, specifically reciting all 1 strand increments within the above-recited range and all ranges formed therein or thereby. In some configurations, the elastic strands 316 may be separated from each other by about 0.4 mm to about 4 mm in the cross direction, specifically reciting all 0.1 mm increments within the above-recited range and all ranges formed therein or thereby. As discussed herein, the elastics in the plurality of elastic strands may be pre-strained prior to joining the elastic strand to the first or second substrate layers 306, 308. In some configurations, the elastic may be pre-strained from about 75% to about 300%, specifically reciting all 1% increments within the above-recited range and all ranges formed therein or thereby. It is also to be appreciated that one or more beams of elastics may be arranged along the cross direction CD of a converting process and/or arranged along a machine direction MD in various different portions of a converting process. It is also to be appreciated that the beam 314 can be connected with one or more motors, such as servo motors, to drive and control the rotation of the beam 314. It is to be appreciated that in some configurations, the elastic strands 316 may be supplied on the beam 314 in a stretched state, and as such, may not require additional stretching (or may require relatively less additional stretching) before being combined with the first substrate 306 and/or the second substrate 308. In some configurations, an elastic strand 316 may be drawn from a single roll utilizing a rolling unwind, such as for example, available from Overend Technologies, Inc.

With continued reference to FIGS. 5 and 6, the advancing elastic strands 316 may be joined with the first substrate 306 and the second substrate 308 to form the elastomeric laminate 302. The elastic laminate 302 may also advance past a bond applicator 500 configured to apply bonds 322 that secure the elastic strands 316 between the first substrate 306 and the second substrate 308. One or more of the elastic strands 316 advancing from the beam 314 may include a spin finish 320. As such, the bonds 322 may be configured to secure the elastic strands 316 between the first and second substrates 306, 308 without having to remove the spin finish 320 from the elastic strands 316. It is also to be appreciated that the methods and apparatuses herein may also be configured to remove the spin finish 320 from the elastic strands 316. Examples of spin finish removal processes and apparatuses are disclosed in U.S. Provisional Patent Application No. 62/483,965, which is incorporated by reference herein. The spin finish removal apparatus may be configured to apply detergent to an advancing elastic strand and may also wipe and/or dry the advancing elastic strand. The treated stretched elastic strand may then be connected between a first substrate and a second substrate. In addition, the elastic laminates 302 herein may be constructed with or without adhesives between the first and second substrates 306, 308. In addition, it is to be appreciated that the bonding methods and apparatuses herein may be utilized in conjunction with other bonding methods and apparatuses, such as disclosed in U.S. Patent Application No. 62/553,149, filed on Sep. 1, 2017, which is incorporated by reference herein.

It is to be appreciated that one or more of the elastic strands 316 may include various types of spin finish 320, also referred herein as yarn finish, configured as coating on the elastic strands 316 that may be intended to help prevent the elastics strands from adhering to themselves, each other, and/or downstream handling equipment. In some configurations, a spin finish may include various types of oils and other components, such as disclosed for example in U.S. Pat. Nos. 8,377,554; 8,093,161; and 6,821,301. In some configurations, a spin finish may include various types of silicone oils, such as for example, polydimethylsiloxane. In some configurations, a spin finish may include various types of mineral oils. It is to be appreciated that the amount of spin finish applied to elastic strands may be optimized depending on the process configuration in which the elastic strands may be used. For example, in process configurations wherein elastic strands have limited contact or do not contact downstream handling equipment, such as idlers, the amount of spin finish may be selected to help prevent the elastics strands from adhering to themselves and/or each other while wound on a beam without regard to whether elastic strands would adhere to downstream handling equipment. As such, it is to be appreciated that the elastic strands herein may include various amounts of spin finish that may be expressed in various ways. For example, a quantity of 10 grams of spin finish per 1 kilogram of elastic strand may be expressed as 1% spin finish. In some configurations, an elastic strand may include about 0.1% spin finish. In some configurations, a strand may include from about 0.01% to about 10% spin finish, specifically reciting all 0.01% increments within the above-recited range and all ranges formed therein or thereby.

As shown in FIG. 6, the bonds 322 may extend for discrete lengths along the machine direction MD and may be intermittently arranged along the machine direction of the elastic laminate 302. Thus, the elastic strands 316 may extend in the machine direction MD between intermittently spaced bond regions 360 and unbonded regions 362. It is to be appreciated that the bonds 322 may extend contiguously for various lengths in the cross direction CD and may extend across one or more elastic strands 316. The bonds 322 may also be separated from each other in the cross direction CD, such as shown for example in FIG. 11.

Figure 7A:
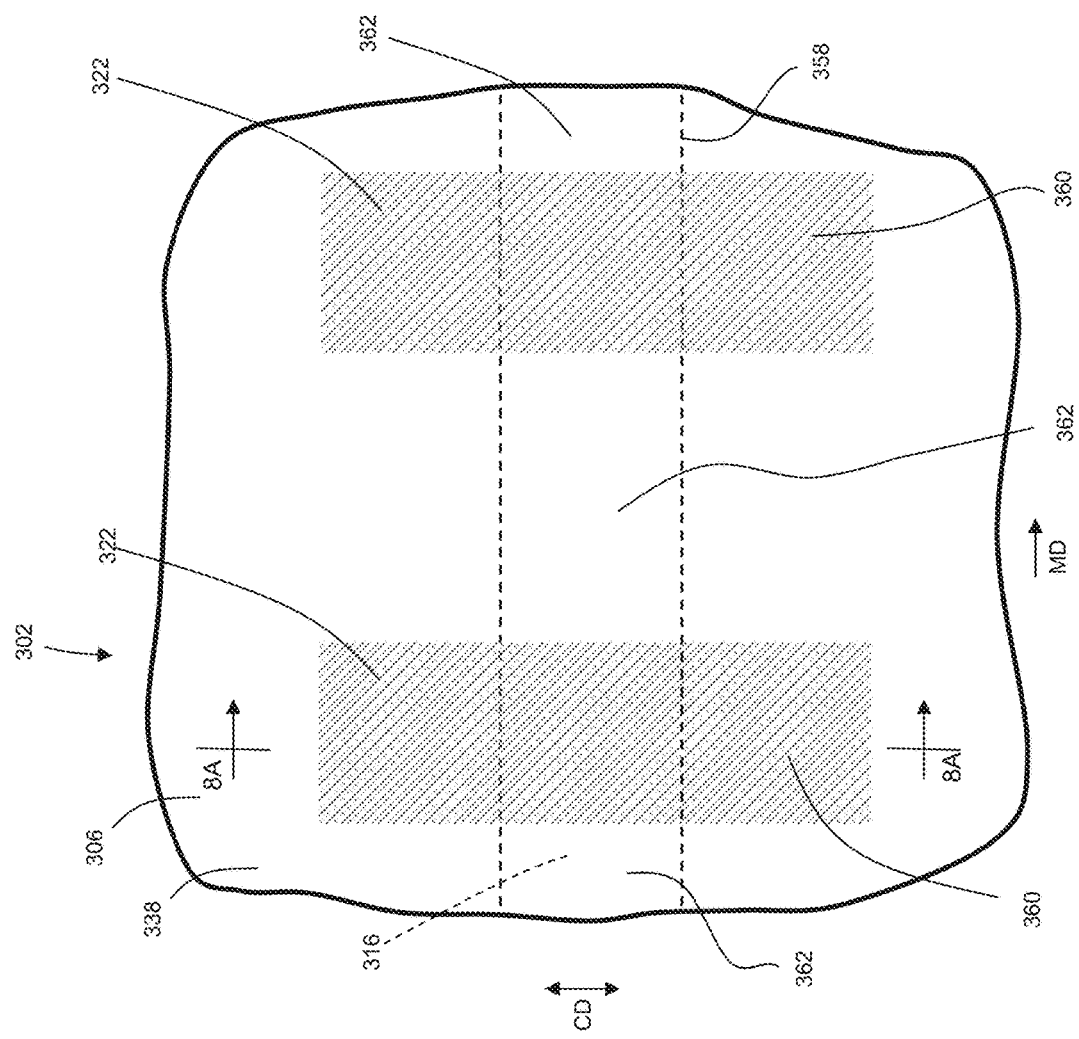
FIG. 7A is a detailed view of an elastic strand in a stretched state bonded between the first and second substrates.
Figure 8A:
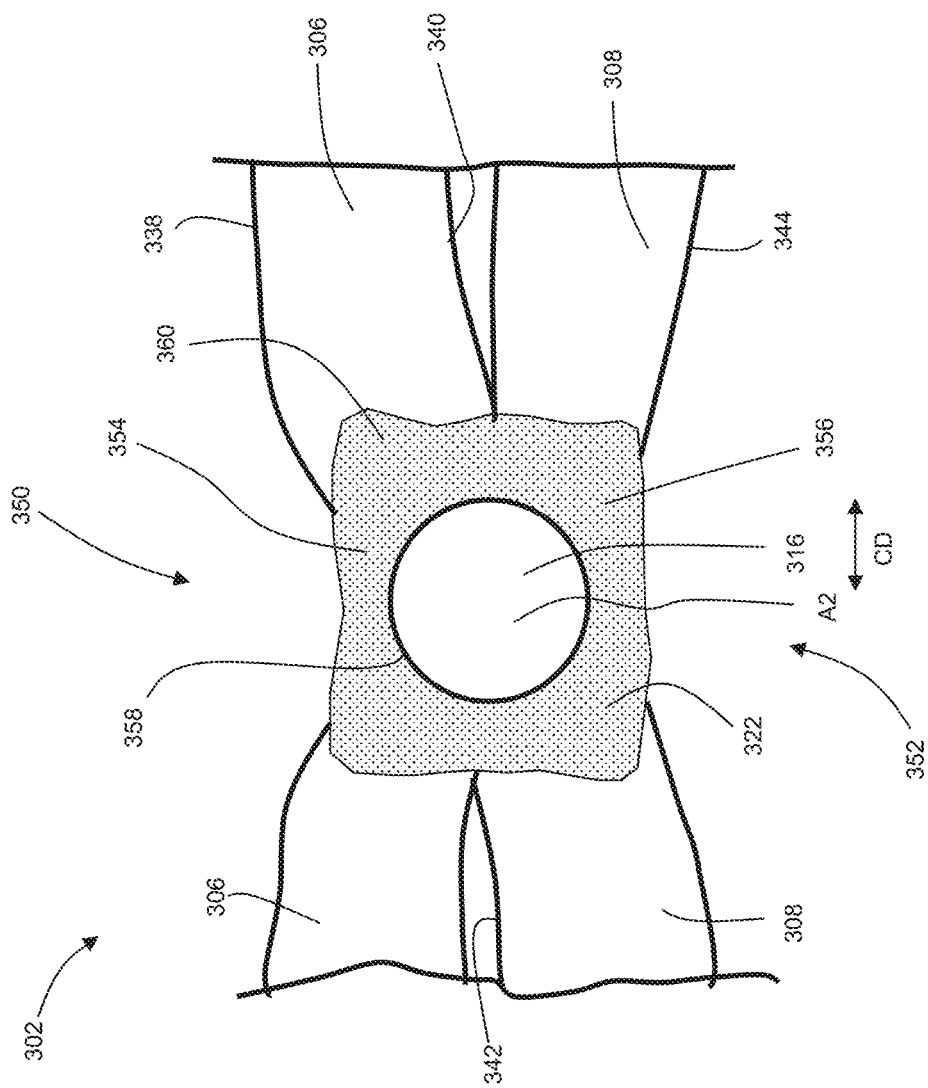
FIG. 8A is a sectional view of the elastic strand, bond, first substrate, and second substrate of FIG. 7A taken along line 8A-8A.

FIGS. 7A and 8A are detailed views of an elastic strand 316 in a stretched state secured with bonds 322 between the first and second substrates 306, 308. During the bonding process, the bond applicator 500 may apply heat and pressure to a first region 350 of the first substrate 306 and a second region 352 of the second substrate 308 such that first material 354 of the first substrate 306 and second material 356 of the second substrate 308 become malleable. In turn, the malleable first and second materials 354, 356 deform and completely surround an outer perimeter 358 of a discrete length of the stretched elastic strand 316 in a bond region 360. The heat and pressure are removed from the first region 350 of the first substrate 306 and the second region 352 of the second substrate 308 as the elastic laminate 302 advances from the bond applicator 500, and as such, the malleable first and second materials 354, 356 harden in a bond 322 that conforms with a cross sectional shape defined by the outer perimeter 358 of the stretched elastic strand 316. In some configurations, an external heat source may be used to generate the heat used in the bonding process, such as with a heated anvil. It is also to be appreciated that heat may be generated solely by the bonding process, such as for example, heat generated by an ultrasonic horn vibration or heat generated by a fusion bonding process, wherein no external heat source is required. In some configurations, tooling used in the bonding process may also be chilled to help provide and/or control the process temperatures at desired levels.

It is to be appreciated that the bond applicator 500 may be configured in various ways, such as for example, heated or unheated patterned and anvil rolls and/or ultrasonic bonding devices. For example, the bond applicator 500 schematically shown in FIGS. 5 and 5A may include an anvil configured as a pattern roll 502 with a pressing surface 504 adjacent the pattern roll 502. The pattern roll 502 may be adapted to rotate about an axis of rotation 506 extending axially in the cross direction CD. During operation, the elastomeric laminate 302 may be partially wrapped onto the pattern roll 502. And the pattern roll 502 rotates about the axis of rotation 506 to advance the elastomeric laminate 302 through a nip 508 between the pattern roll 502 and the pressing surface 504. As shown in FIG. 5, the bond applicator 500 may also include one or more rolls 503 that help guide the elastomeric laminate to and from the pattern roll 502. The pattern roll 502 may also comprise one or more bonding surfaces 510, also referred to herein as pattern surfaces, defined by one or more bonding elements 512, also referred to herein as pattern elements, extending radially outward from an outer circumferential surface 514. As the elastomeric laminate 302 is advanced between the bonding surface 510 and the pressing surface 504, the first substrate 306 and the second substrate 308 are welded together to create bonds 322 between the first substrate 306 and the second substrate 308.

During the assembly operation, the elastomeric laminate 302 may be partially wrapped onto the pattern roll 502. As shown in FIG. 5, the extent that the elastomeric laminate 302 wraps around the pattern roll 502 is referred to herein as the wrap angle, $\theta$, and may be expressed in units of degrees. In some configurations, the wrap angle, $\theta$, may be greater than zero degrees and less than or equal to 180 degrees, specifically reciting all 1 degree increments within the above-recited range and all ranges formed therein or thereby. In some configurations, the wrap angle, $\theta$, may be greater 180 degrees.

It is to be appreciated that various operational abnormalities may result while elastic strands 316 are advancing from a beam 314 during assembly operations disclosed herein. For example, breakouts may occur during assembly operations, wherein one or more elastic strands 316 unintentionally breaks while advancing from the beam 314 during assembly of the elastomeric laminate 302. The methods and apparatuses herein may be configured to help isolate broken elastic strands and rethread broken elastic strands. For example, as discussed above with reference to FIG. 5, the elastomeric laminate 302 may be partially wrapped onto the pattern roll 502 for a partial wrap angle, $\theta 1$, before advancing through the nip 508. As such, elastic strands 316 that may be unintentionally broken at the nip 508 may begin to retract upstream from the nip. However, at relatively higher advancement speeds S1, there is less time for the broken elastic strand to retract. As such, the broken elastic strand may be pulled forward while sandwiched between the advancing first and second substrates 306, 308 through the nip 508 at a speed that is greater than the rate of retraction. In turn, the broken elastic strand 316 may be automatically rethreaded. A control parameter to help mitigate elastic retraction would be the size of the partial wrap angle, $\theta 1$, and the web tension.

Figure 5A:
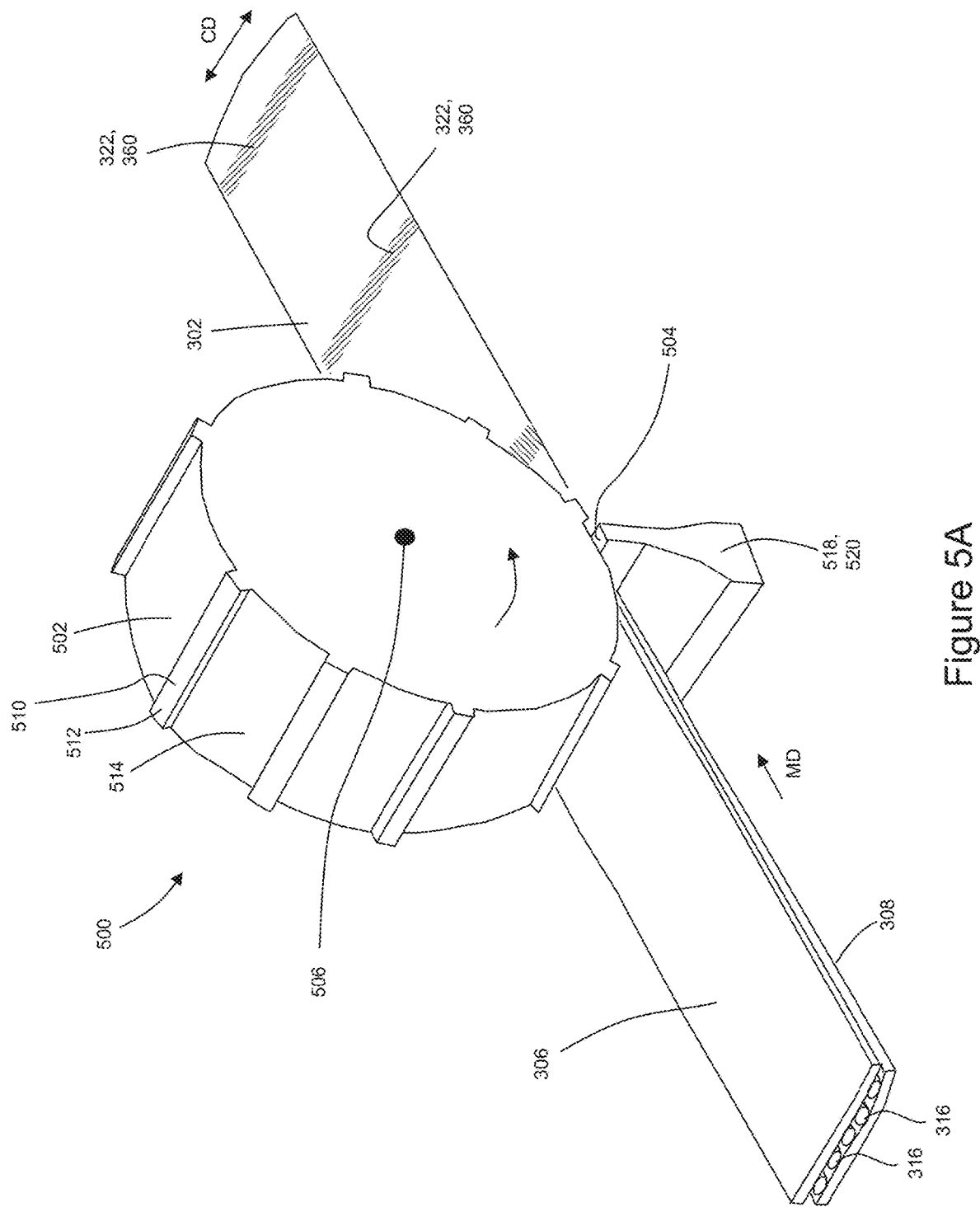
FIG. 5A is a detailed view of an example bonding apparatus configured with an anvil and ultrasonic horn.

It is to be appreciated that the pressing surface 504 may be configured in various ways. For example, as shown in FIGS. 5 and 5A, the pressing surface 504 may comprise an energy transfer surface of an ultrasonic bonding device 518. As such, the bond applicator 500 may include a horn 520 and may be configured to impart ultrasonic energy to the combined substrates 306, 308 and elastic strands 316 on the pattern roll 502. The ultrasonic bonding device 518 may apply energy to the horn 520 to create resonance of the horn 520 at frequencies and amplitudes so the horn vibrates rapidly in a direction generally perpendicular to the substrates 306, 308 and elastic strands 316 being advanced past the horn 520 on the pattern roll 502. Vibration of the horn 520 creates bonds 322 and/or bond regions 360 by generating heat to melt and bond the substrates 306, 308 together in areas supported by the bonding surface 510 on the pattern roll 502. Thus, the bonds 322 and/or bond regions 360 may have shapes that correspond with and may mirror shape of the bonding surfaces 510. As shown in FIG. 5A, the pattern surface 510 may extend contiguously across one or more elastic strands 316 positioned between the first substrate 306, and the second substrate 308.

It is to be appreciated that the number, size, and shape of some or all the pattern surfaces 510 and/or pattern elements 512 may be different. In some configurations, the shape and size of the pattern surface 510 of each pattern element 512 may be identical or substantially identical to each other. In some configurations, the pattern elements 512 and/or pattern surfaces 510 may have a perimeter that defines circular, square, rectangular, elliptical, and various types of other shapes. In some configurations, the anvil 502 may include a pattern element 512 with a pattern surface 510 that defines a continuous crossing line pattern and/or various other shapes, such as disclosed in U.S. Pat. No. 9,265,672, which is incorporated by reference herein. It is to be appreciated that the choice of pattern surface shape may enable the creation of unique textures and patterns where the location and size of the bonding sites impact local buckling resistance of a nonwoven laminate and may create desired homogeneous textures upon relaxation of the elastics and the resulting nonwoven corrugation. It is also to be appreciated that the pattern elements 512 and comprise pattern surfaces with chamfered or radial, curved edges.

Some bond applicators may be configured to a maintain relatively constant distance between the pressing surface 504 and the pattern surface 510. For example, some ultrasonic bonding devices 518 may be configured to move the horn 520 toward and away from the pattern surface 510 to help maintain a relatively constant distance between them. To help maintain relatively consistent bond quality without cutting the elastic strands 316, the speeds at which such a horn 520 would have to move back and forth increases as speeds at which the substrates 306, 308 and elastic strands 316 advance through the nip 508. Pattern rolls 502 with comprising relatively small runout values may help mitigate requirements for such increased speeds of horn 520 movement. As such, it is to be appreciated that the pattern roll 502 may be configured with pattern surfaces 510 extending for various lengths in the cross direction CD and comprising various total runout values. For example, in some configurations, the pattern roll 502 may include pattern surfaces 510 extending in the cross direction for a length of at least about 100 mm. In some configurations, the pattern roll 502 may include pattern surfaces 510 comprising total runout values ranging from about 0 μm ("microns") to about 10 μm, specifically reciting all 1 μm increments within the above-recited range and all ranges formed therein or thereby. The term "total runout" refers herein to the total runout as defined in ASME Y14.5-2009.

It is to be appreciated that aspects of the ultrasonic bonding devices 518 may be configured in various ways, such as for example linear or rotary type configurations, and such as disclosed for example in U.S. Pat. Nos. 3,113,225; 3,562,041; 3,733,238; 5,110,403; 6,036,796; 6,508,641; and 6,645,330. In some configurations, the ultrasonic bonding device 518 may be configured as a linear oscillating type sonotrode, such as for example, available from Herrmann Ultrasonic, Inc. In some configurations, the sonotrode may include a plurality of sonotrodes nested together in the cross direction CD. The bond applicator 500 may also be configured in various other ways, such as for example, the mechanical bonding devices and methods disclosed in U.S. Pat. Nos. 4,854,984; 6,248,195; 8,778,127; and 9,005,392; and U.S. Patent Publication Nos. 2014/0377513 A1; and 2014/0377506 A1. Although the bond applicator 500 is shown in FIGS. 5 and 6 as a separate device that is positioned downstream of the second metering device 312, it is to be appreciated the second metering device 312 may also be configured as the bond applicator 500. As such, the first substrate 306, second substrate 308, and elastic strands 316 may be combined and bonded together at the bond applicator 500 to form the elastic laminate 302.

It is to be appreciated that the combined first substrate 306, second substrate 308, and elastic strands 316 may advance at various speeds S1 through the bonding process. For example, in some configurations, the combined first substrate 306, second substrate 308, and elastic strands 316 may advance in the machine direction MD through the nip 508 between the pattern roll 502 and the pressing surface 504 at speeds ranging from about 100 meters per minute to about 450 meters per minute, specifically reciting all 1 meter per minute increments within the above-recited range and all ranges formed therein or thereby.

Figure 7B:
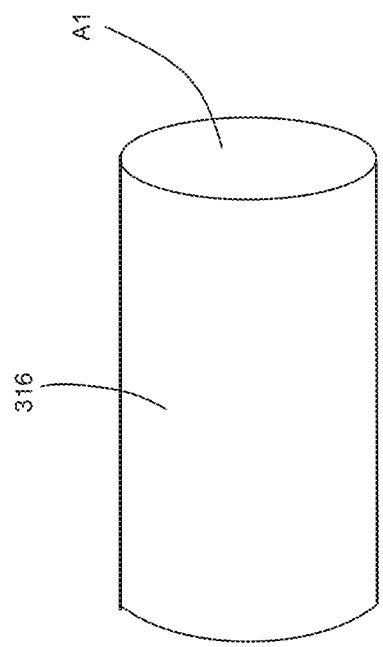
FIG. 7B shows a length of an elastic strand in a relaxed state with a first cross sectional area.
Figure 7C:
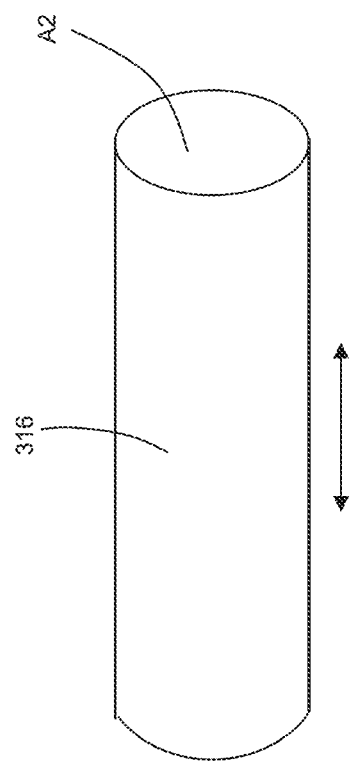
FIG. 7C shows a length of the elastic strand of FIG. 7B in a stretched state with a second cross sectional area that is less than the first cross sectional area.

As previously mentioned, a frictional lock may be applied between a portion of the elastic strand 316 and the hardened first and second materials 354, 356 by releasing tension from the stretched elastic strand 316. The frictional lock acts to hold and/or secure the elastic strand 316 in a fixed position in the bond region 360. For the purposes of a general explanation, FIG. 7B shows a length of an elastic strand 316 in a unstretched or relaxed state, wherein the elastic strand 316 defines a first cross sectional area A1. And FIG. 7C shows a length of the elastic strand 316 from FIG. 7B in a stretched state, wherein the elastic strand 316 defines a second cross sectional area A2 that is less than the first cross sectional area A1. Thus, the cross sectional area of the stretched elastic strand 316 expands when tension is partially or fully released from the elastic strand 316. As discussed in more detail below, the tendency of the cross sectional area of the elastic strand 316 to expand helps create the frictional lock.

Figure 7D:
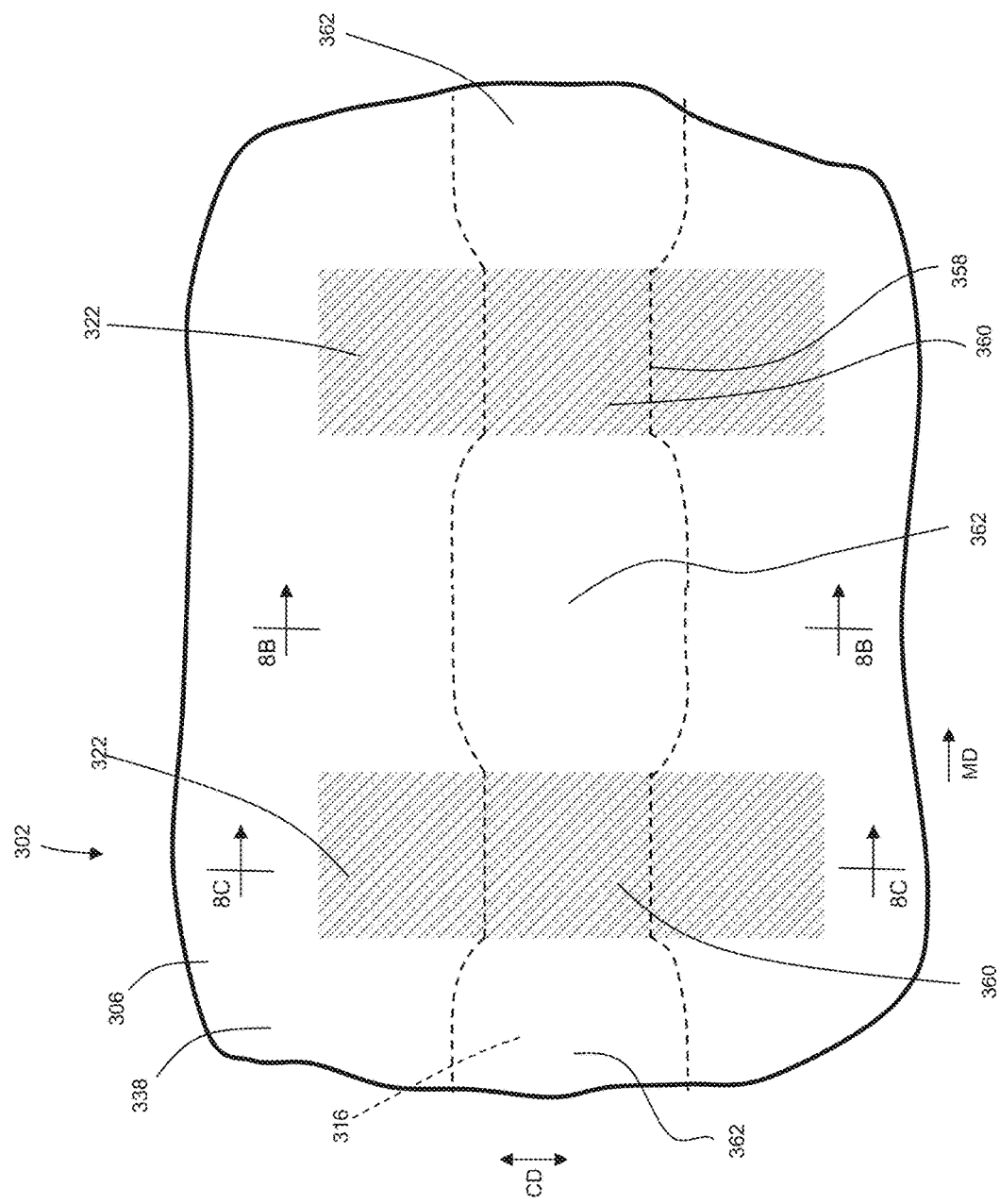
FIG. 7D is a detailed view of an elastic strand in a relaxed state bonded between the first and second substrates.
Figure 8B:
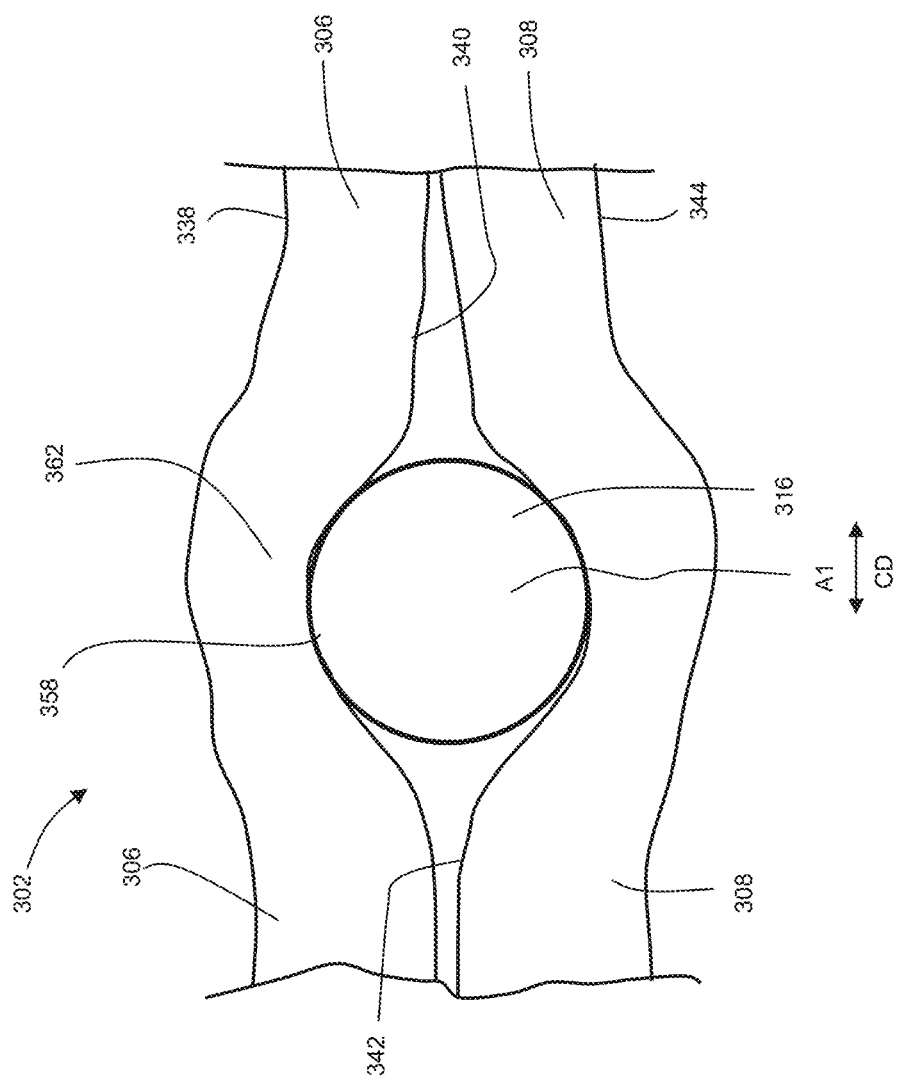
FIG. 8B is a sectional view of the elastic strand in an unbonded region of FIG. 7D taken along line 8B-8B, wherein the elastic strand is in a relaxed state.

Turning next to FIG. 7D, a detailed view of an elastic strand 316, such as shown in FIG. 7A, is provided wherein tension has been released (or reduced) on the elastic strand 316 and showing how the tendency of the elastic strand 316 to expand creates a frictional lock in the bonded region 360. FIGS. 7D and 8B show the elastic strand 316 as having a first cross sectional area A1 in an unbonded region 362 of the elastic laminate 302, wherein the first cross sectional area A1 is greater than the second cross sectional area A2 of the stretched elastic strand 316 shown in FIGS. 7A and 8A. And FIGS. 7D and 8C show the elastic strand 316 as having a third cross sectional area A3 in the bond region 360 of the elastic laminate 302, wherein the third cross sectional area A3 is the same or about the same as the second cross sectional area A2 of the stretched elastic strand 316 shown in FIGS. 7A and 8A. As shown in FIG. 8C, the hardened first and second materials 354, 356 in the bond region 360 help prevent the cross sectional area of the elastic strand 316 from expanding when tension has on elastic strand 316 has been reduced. The tendency of the elastic strand 316 to expand creates forces F (represented by dashed double arrow lines in FIG. 8C) exerted between the hardened first and second materials 354, 356 in the bond region 360. In turn, the forces F between the elastic strand 316 and the hardened first and second materials 354, 356 creates a frictional lock by increasing the friction forces between the elastic strand 316 and the hardened materials 354, 356. The increased friction forces in the machine direction MD along the length of the elastic strand 316 in the bond region 360 holds the discrete length of the elastic strand 316 in a fixed position in the bond region 360 together with the first and second substrates 306, 308. As such, in some configurations, no adhesive may be applied to and/or present between the elastic strand 316 and the hardened materials 354, 356. It is also to be appreciated that in some configurations, adhesive may be applied to and/or present between the elastic strand 316 and the hardened materials 354, 356 to help the frictional lock hold the discrete length of the elastic strand 316 in a fixed position in the bond region 360 together with the first and second substrates 306, 308. In some configurations, adhesive and the frictional lock in the bond regions 360 may share the load exerted by elastic strand 316. In some configurations, adhesive positioned on the elastic strand 316 may increase the coefficient of friction between the elastic strand 316 and the hardened materials 354, 356 in the bond region 360. It is to be appreciated that various quantities of adhesive may be present in the bond regions 360, such as for example, about 10 gsm or less.

Figure 9A:
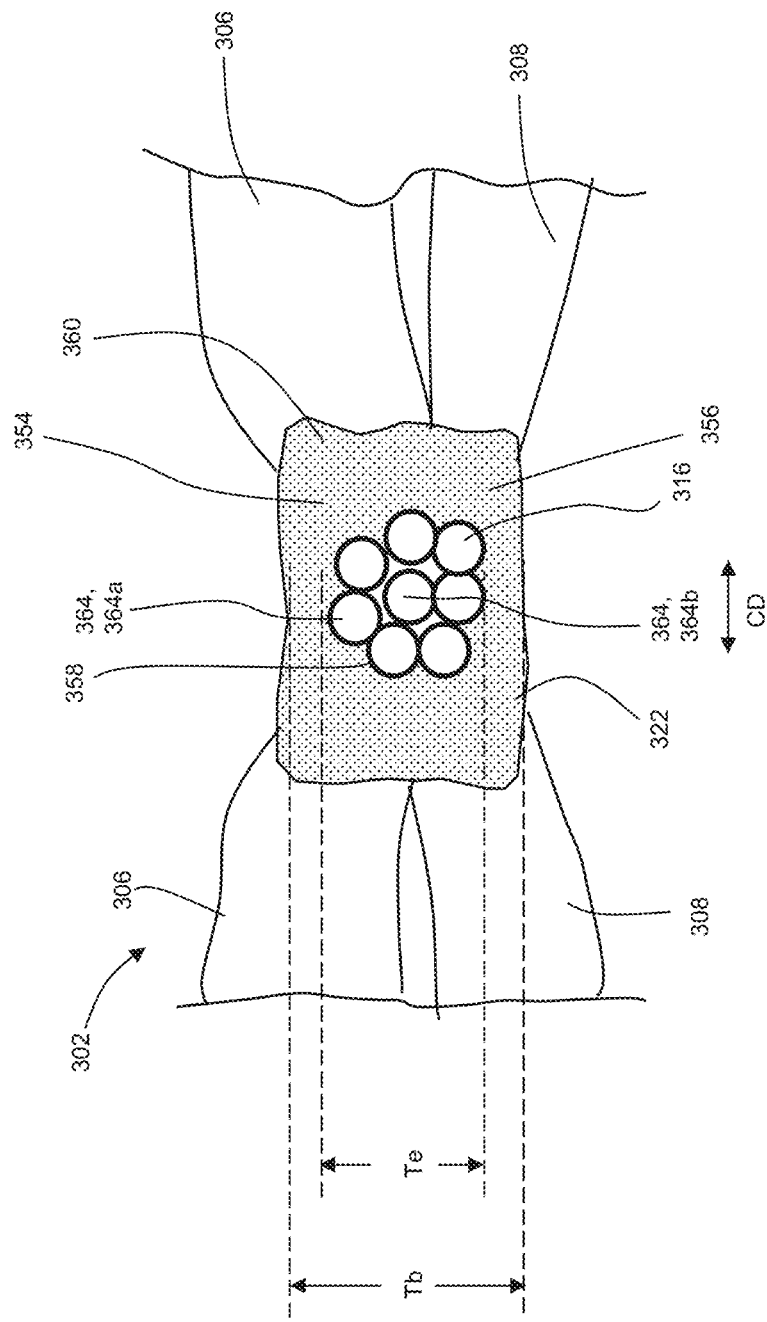
FIG. 9A is a sectional view of an elastic strand, bond, first substrate, and second substrate of FIG. 7A taken along line 8A-8A, wherein a plurality of filaments of the elastic strand are bonded in a first configuration.

It is also to be appreciated that the elastic strands 316 herein bonded in accordance with the methods described herein may also be constructed from one or more filaments 364. For example, FIG. 9A shows a cross sectional view of an elastic strand 316 in a bond region 360 wherein the elastic strand 316 comprises a plurality of individual filaments 364. As shown in FIG. 9A, the elastics strand 316 includes outer filaments 364a surrounding an inner filament 364b. The outer filaments 364a define the outer perimeter 358 of the elastic strand 316, and the outer filaments 364a may surround the inner filament 364b such that the inner filament 364b is not in contact with the hardened first material 354 and the hardened second material 356 in the bond 322. It is to be appreciated that the filaments 364 may be arranged in various positions within the bond region 360. For example, FIG. 9B shows a cross sectional view of an elastic strand 316 in a bond region 360 wherein the plurality of individual filaments 364 together define a perimeter 358 that is elongated along the cross direction CD, and wherein all of the plurality of filaments 364 are in contact with hardened first material 354 and hardened second material 356. In another example, FIG. 9C shows a cross sectional view of an elastic strand 316 in a bond region 360 wherein at least two of the filaments 364 are separated from each other by at least one of hardened first material 354 and hardened second material 356.

It is to be appreciated that different components may be used to construct the elastomeric laminates 302 in accordance with the methods and apparatuses herein. For example, the first and/or second substrates 306, 308 may include nonwovens and/or films and may be constructed from various types of materials, such as plastic films; apertured plastic films; woven or nonwoven webs of natural materials, such as wood or cotton fibers; synthetic fibers, such as polyolefins, polyamides, polyester, polyethylene, or polypropylene fibers or a combination of natural and/or synthetic fibers; or coated woven or nonwoven webs; polymeric films such as thermoplastic films of polyethylene or polypropylene, and/or a multi-layer or composite materials comprising a film and a nonwoven material. In some configurations, the first and/or second substrates 306, 308 may include nonwovens configured with basis weight values of at least about 10 gsm, and may include nonwovens configured with basis weight values ranging from about 10 gsm to about 30 gsm, specifically reciting all 1 gsm increments within the above-recited range and all ranges formed therein or thereby.

It is also to be appreciated that the strands 316 and/or filaments 364 herein may define various different cross-sectional shapes. For example, in some configurations, strands 316 or filaments 364 may define circular, oval, or elliptical cross sectional shapes or irregular shapes, such as dog bone and hourglass shapes. In addition, the elastic strands 316 may be configured in various ways and with various decitex values. In some configurations, the elastic strands 316 may be configured with decitex values ranging from about 40 decitex to about 150 decitex, and may be configured with decitex values ranging from about 10 decitex to about 500 decitex, specifically reciting all 1 decitex increments within the above-recited range and all ranges formed therein or thereby.

As previously mentioned, substrates 306, 308 with elastic strands 316 positioned therebetween can be bonded in accordance with methods herein without severing the elastics strands and without the need for nesting grooves in bond applicator 500. For example, as shown in FIGS. 8C and 9A-9C, heat and pressure may be applied to the substrates 306, 308 to create bonds 322 surrounding the elastic strand 316. The bond 322 is defined by hardened first material 354 and hardened second material 356 and has a minimum thickness Tb. In addition, the elastic strand 316 may have a thickness Te in the bond region 360. In some configurations, substrates 306, 308 that are bonded together to create a bond thickness Tb having a certain size relative to the elastic strand thickness Te, the elastic strand 316 may not be severed during the bonding process. In addition, the forces F exerted between the elastic strand 316 and the hardened first and second materials 354, 356 in the bond region 360 may be prevented from breaking the bond 322. Such a relationship between Te and Tb may be characterized by the decitex of elastic strands 316 and the bond thickness Tb. For example, substrates 306, 308 may be bonded together with an elastic strand having a decitex value less than or equal to about 70 positioned therebetween to create a bond 322 having a thickness Tb of at least about 100 μm ("microns") without severing the elastic strand 316. In another example, substrates 306, 308 may be bonded together with an elastic strand having a decitex value less than or equal to about 250 positioned therebetween to create a bond 322 having a thickness Tb of at least about 200 μm ("microns") without severing the elastic strand 316. In some configurations, such as shown in FIG. 9C, the bond thickness Tb may be at least 50% larger than the minimum cross sectional thickness Tf a filament 364. For example, as shown in FIG. 9C, the minimum cross sectional thickness Tf of a filament 364 having a circular cross section may be defined the diameter of such a filament.

Figure 9D:
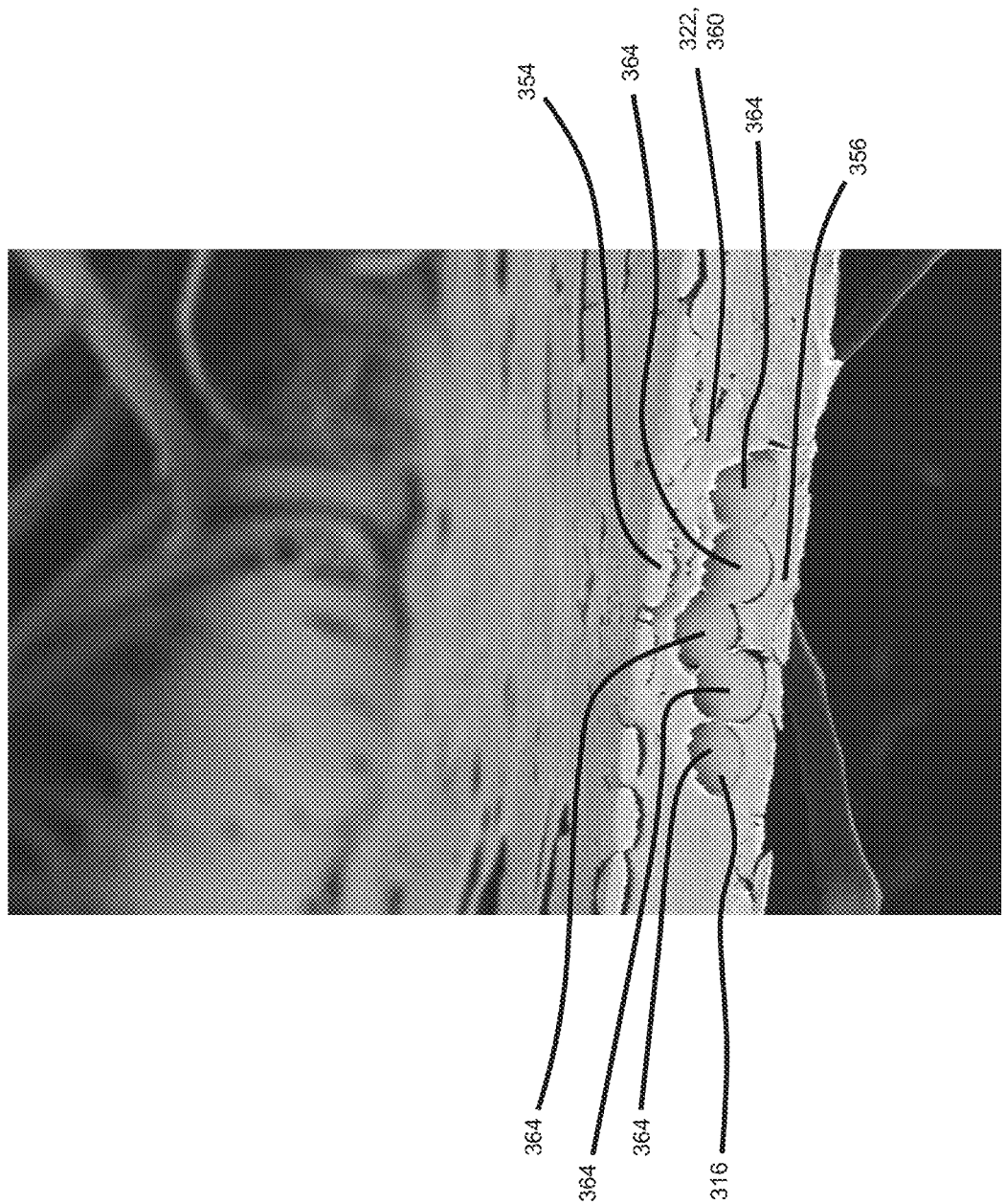
FIG. 9D is a scanning electron microscope ("SEM") photograph of a cross sectional view of an elastic strand including five filaments in a bonded region and surrounded by hardened first and second materials.
Figure 9E:
FIG. 9E is a scanning electron microscope ("SEM") photograph of a cross sectional view of an elastic strand including five filaments in a bonded region and surrounded by hardened first and second materials.
Figure 9F:
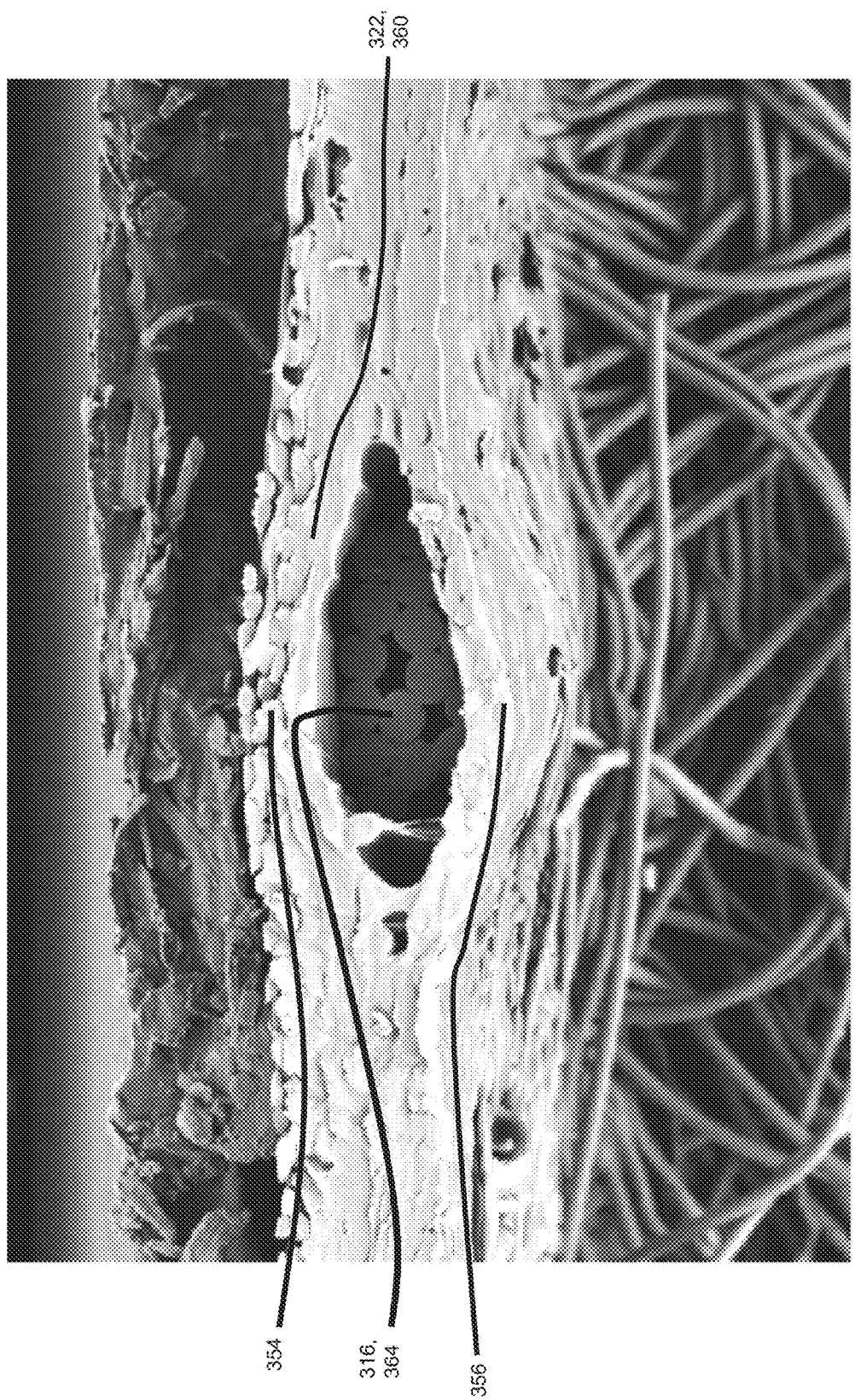
FIG. 9F is a scanning electron microscope ("SEM") photograph of a cross sectional view of an elastic strand including fifteen filaments in a bonded region and surrounded by hardened first and second materials.

FIGS. 9D-9F electron microscope photographs ("SEM") showing cross sectional views of an elastic strand 316 in a bond region 360 surrounded by hardened first and second materials 354, 356 from two nonwovens. In FIGS. 9D and 9E, the elastic strand 316 is a 70 decitex elastic strand including five filaments 364, wherein each filament 364 has a diameter of about 43 μm ("microns"). And the bond 322 defines a thickness Tb of about 80 μm ("microns"). In FIG. 9F, the elastic strand 316 is a 235 decitex elastic strand including fifteen filaments 364, wherein each filament 364 has a diameter of about 43 μm ("microns"). And the bond 322 defines a thickness Tb of about 200 μm ("microns").

Figure 10:
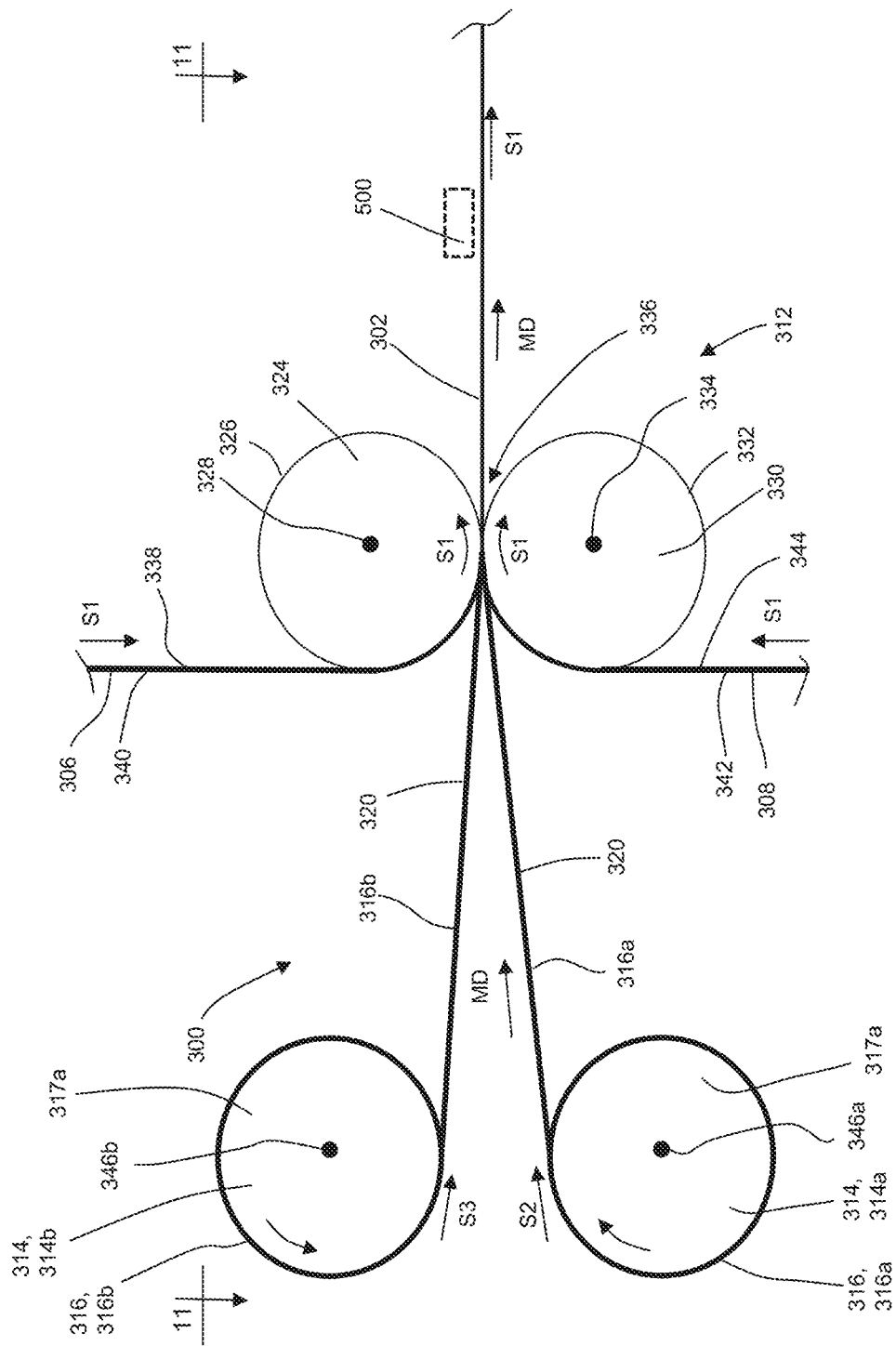
FIG. 10 is a schematic side view of a second configuration of a converting apparatus joining elastic strands between a first substrate and a second substrate, wherein the elastic strands drawn from different beams are stretched to have different elongations.
Figure 11:
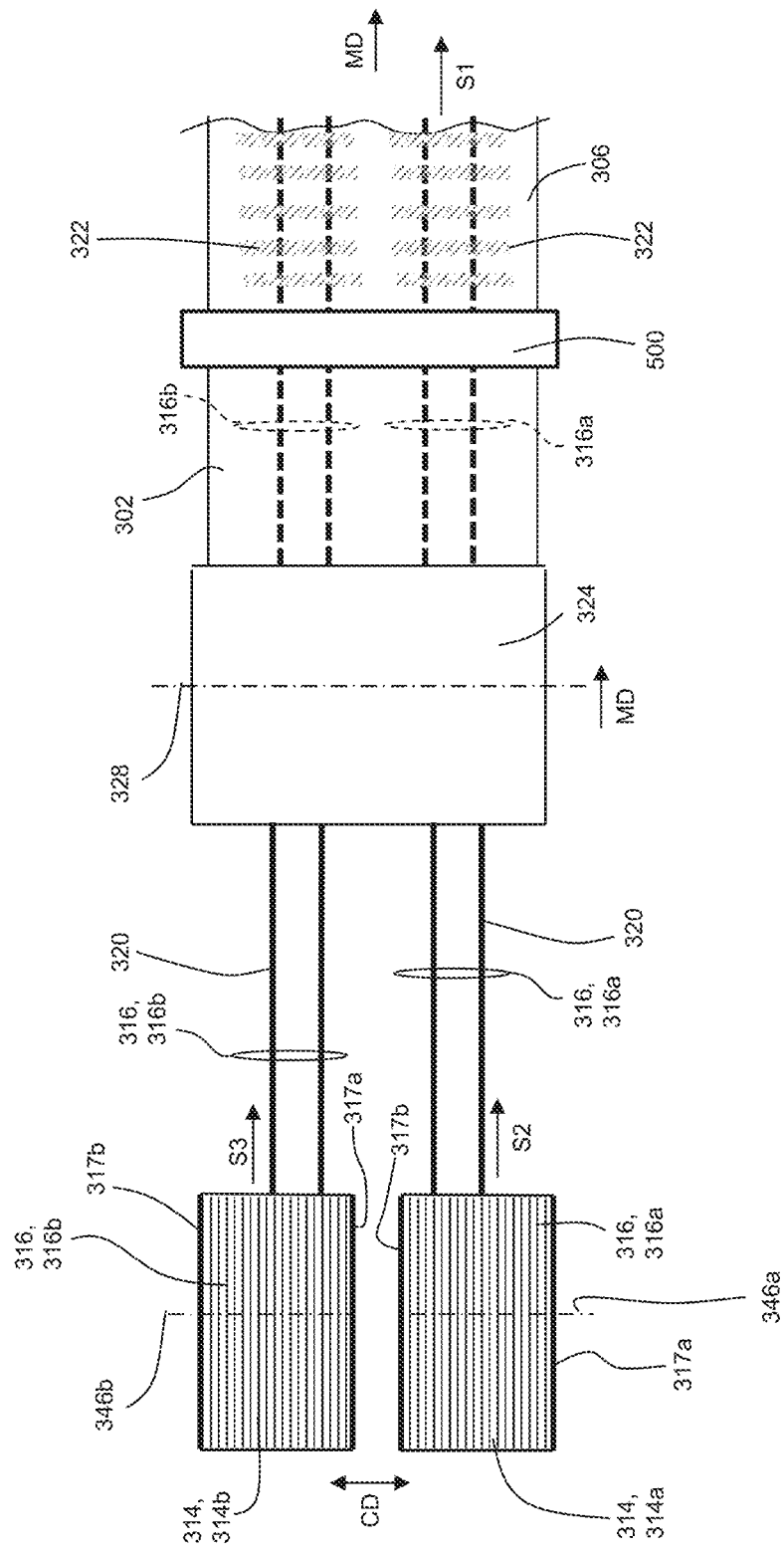
FIG. 11 is a view of the converting apparatus of FIG. 10 taken along line 11-11.

It is to be appreciated that the apparatuses 300 herein may be configured in various ways with various features described herein to assemble elastomeric laminates 302 having various stretch characteristics. For example, the apparatus 300 may be configured to assemble elastomeric laminates 302 with elastic strands 316 unwound from more than one beam and/or in combination with elastic stands supplied from an overend or surface driven unwinder. For example, FIGS. 10 and 11 illustrate the apparatus 300 configured to assemble elastomeric laminates 302 with elastic strands 316 unwound from more than one beam 314. In particular, the apparatus 300 may include a first beam 314a with first elastic strands 316a wound thereon and a second beam 314b with second elastic strands 316b wound thereon. The first beam 314a is rotatable about a first beam rotation axis 346a, and the second beam 314b is rotatable about a second beam rotation axis 346b. During operation, as the first beam 314a rotates, the first elastic strands 316a advance in the machine direction MD from the first beam 314a at a speed S2 with the first elastic strands 316a being spaced apart from each other in the cross direction CD. From the first beam 314a, the first elastic strands 316a advance in the machine direction MD and are joined with the first substrate 306 and the second substrate 308 as discussed above. Similarly, as the second beam 314b rotates, the second elastic strands 316b advance in the machine direction MD from the second beam 314b at a speed S3 with the second elastic strands 316b being spaced apart from each other in the cross direction CD. From the second beam 314b, the second elastic strands 316b advance in the machine direction MD and are joined with the first substrate 306 and the second substrate 308 as discussed above. It is also to be appreciated that the apparatus configuration shown in FIGS. 10 and 11 may also include the bond applicator 500 arranged to apply the bonds 322 as discussed above. The bond applicator 500 is generically represented by a dashed-line rectangle in FIG. 10.

With continued reference to FIGS. 10 and 11, the elastic strands 316a, 316b may be joined with the first and second substrates 306, 308 such that the elastomeric laminate 302 may have different stretch characteristics in different regions along the cross direction CD. For example, when the elastomeric laminate 302 is elongated, the first elastic strands 316a may exert contraction forces in the machine direction MD that are different from contraction forces exerted by the second elastic strands 316b. Such differential stretch characteristics can be achieved by stretching the first elastic strands 316a more or less than the second elastic strands 316b before joining the elastic strands 316a, 316b with the first and second substrates 306, 308. For example, as previously discussed, the first substrate 306 and the second substrate 308 may each advance at a speed S1. In some configurations, the first elastic strands 316a may advance from the first beam 314a at speed S2 that is less than the speed S1, and second elastic strands 316b may advance from the second beam 314b at the speed S3 that is less than the speed S1. As such, the first elastic strands 316a and the second elastic strands 316b are stretched in the machine direction MD when combined with the first and second substrates 306, 308. In addition, the speed S2 may be less than or greater than different than the speed S3. Thus, the first elastic strands 316a may be stretched more or less than the second elastic strands 316b when combined with the first and second substrates 306, 308. It is also appreciated that the first and second elastic strands 316a, 316b may have various different material constructions and/or decitex values to create elastomeric laminates 302 having different stretch characteristics in different regions. In some configurations, the elastic laminate may have regions where the elastic strands 316 are spaced relatively close to one another in the cross direction CD and other regions where the elastic strands 316 are spaced relatively farther apart from each other in the cross direction CD to create different stretch characteristics in different regions. In some configurations, the elastic strands 316 may be supplied on the beam 314 in a stretched state, and as such, may not require additional stretching (or may require relatively less additional stretching) before being combined with the first substrate 306 and/or the second substrate 308. Thus, in some configurations, the first elastic strands 316a may be supplied on the first beam 314a at a first tension, and the second elastic strands 316b may be supplied on the second beam 314b at a second tension, wherein the first tension is not equal to the second tension.

Figure 12:
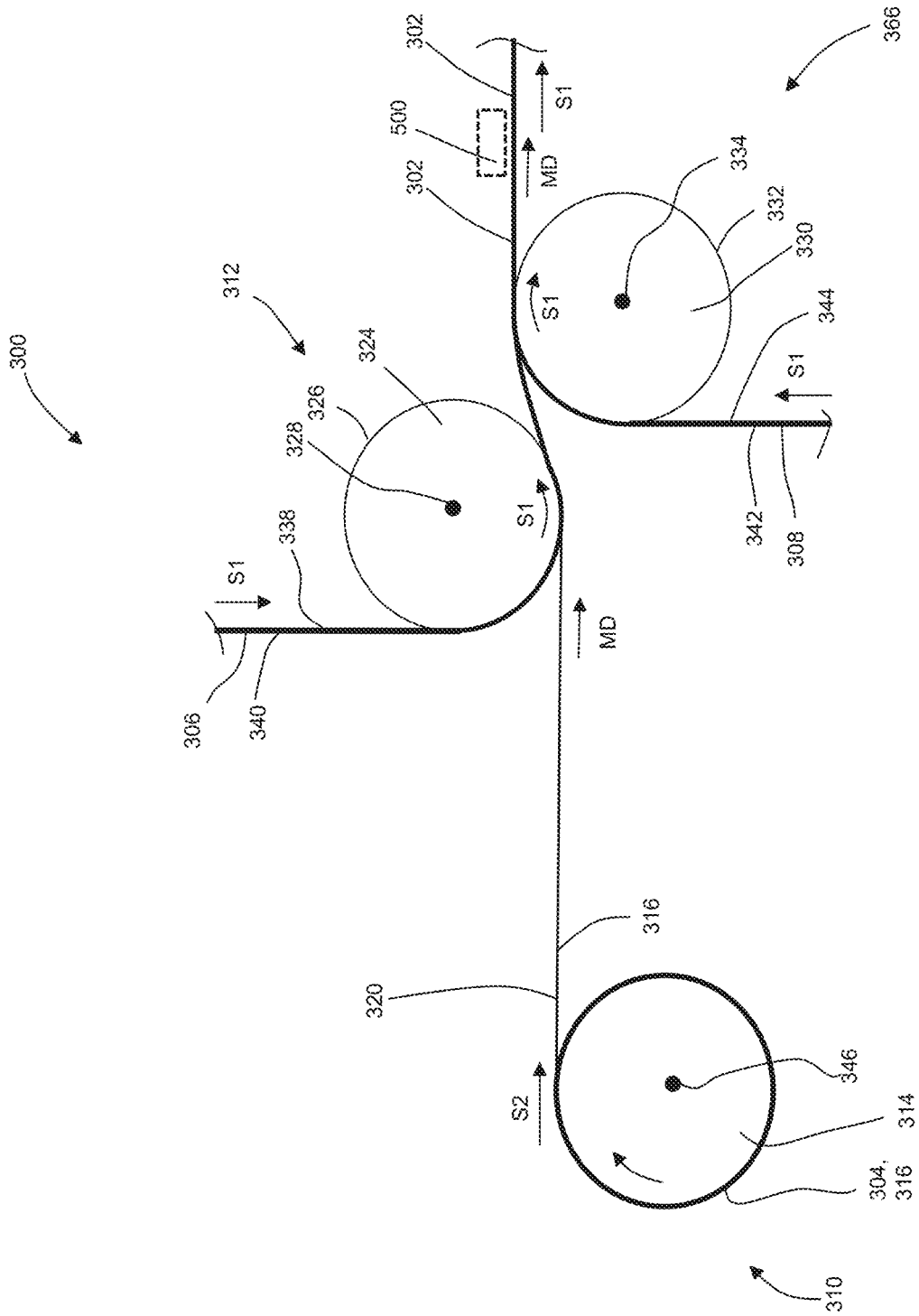
FIG. 12 is a schematic side view of a third configuration of a converting apparatus adapted to manufacture an elastomeric laminate.
Figure 14:
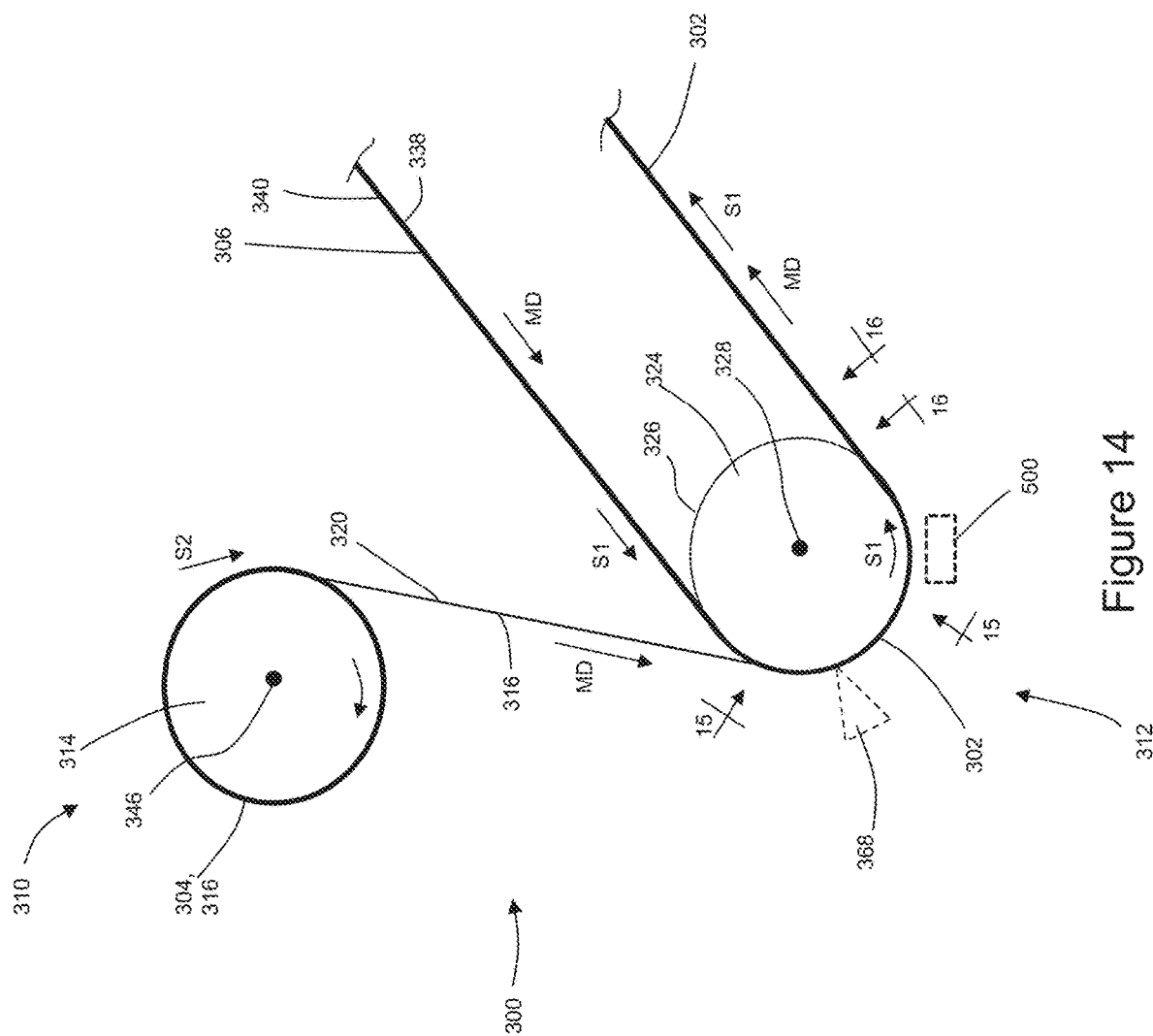
FIG. 14 is a schematic side view of a fifth configuration of a converting apparatus adapted to manufacture an elastomeric laminate.

In another configuration shown in FIG. 12, the second roller 330 may be positioned downstream from the first roller 324. As such, the first roller 324 may be configured as the second metering device 312 and the second roller 330 may be configured as a third metering device 366. As shown in FIG. 14, the first substrate 306 advances at speed S1 to the first roller 324 where the first substrate 306 partially wraps around the outer circumferential surface 326 of the first roller 324 and advances from the first roller to the second roller 330 to be combined with second substrate 308. As the beam 314 rotates, the elastic strands 316 advance from the beam 314 at a speed S2 with the elastic strands 316 being spaced apart from each other in the cross direction CD. From the beam 314, elastic strands 316 advance to the first roller 324 and are positioned on the second surface 340 of the first substrate 306. In some configurations, the speed S2 is less than the speed S1, and as such, the elastic strands 316 are stretched in the machine direction MD. With continued reference to FIG. 12, the first substrate 306 and the elastic strands 316 advance from the outer circumferential surface 326 of the first roller 324 to the second roller 330. In addition, the second substrate 308 advances at speed S1 to the second roller 330 where the second substrate 308 partially wraps around the outer circumferential surface 332 of the second roller 330. In turn, the combined first substrate 306 and the stretched elastic strands 316 advance from first roller 324 to the second roller 330 and are combined with the second substrate 308 such that the elastic strands 316 are joined with the second surface 340 of the first substrate 306 and the first surface 342 of the second substrate 308 to produce a continuous length of elastomeric laminate 302.

Figure 13:
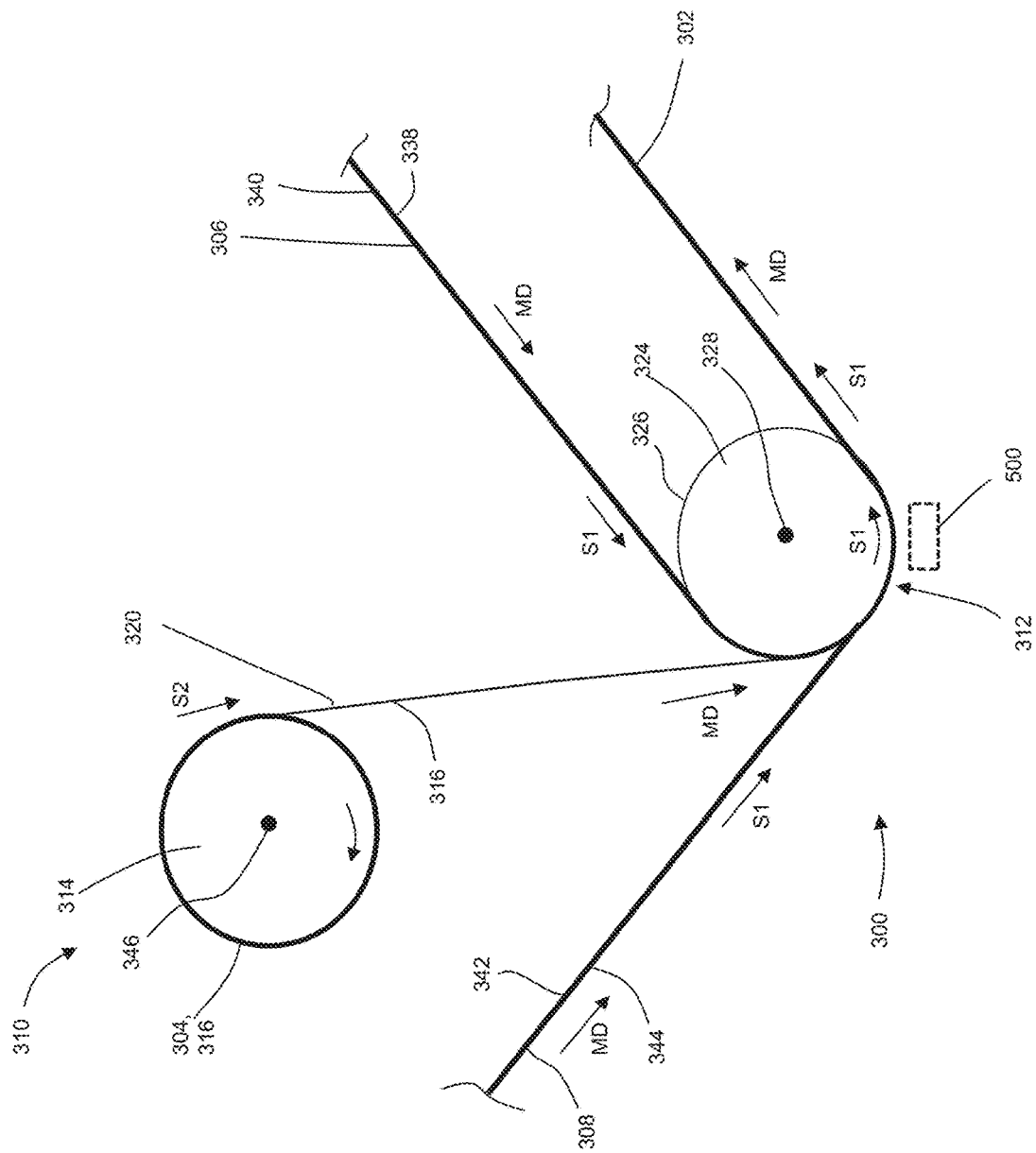
FIG. 13 is a schematic side view of a fourth configuration of a converting apparatus adapted to manufacture an elastomeric laminate.

In another configuration shown in FIG. 13, the apparatus 300 may be configured with only the first roller 324 and without a second roller 330. As such, the first roller 324 may be configured as the second metering device 312. In addition, the first roller 324 may also be configured as a component of the bond applicator 500. As shown in FIG. 13, the first substrate 306 advances at speed S1 to the first roller 324 where the first substrate 306 partially wraps around the outer circumferential surface 326 of the first roller 324. While partially wrapped around the outer circumferential surface 326 of the first roller 324, the first substrate 306 is combined with the elastic strands 316 and the second substrate 308. As the beam 314 rotates, the elastic strands 316 advance from the beam 314 at a speed S2 with the elastic strands 316 being spaced apart from each other in the cross direction CD. From the beam 314, elastic strands 316 advance to the first roller 324 and are positioned on the second surface 340 of the first substrate 306. In some configurations, the speed S2 is less than the speed S1, and as such, the elastic strands 316 are stretched in the machine direction MD. With continued reference to FIG. 13, the second substrate 308 advances at speed S1 to the first roller 324 and partially wraps around the outer circumferential surface 326 of the first roller 324. In turn, the second substrate 308 is combined with the first substrate 306 and the stretched elastic strands 316 while on the first roller 324 such that the elastic strands 316 are joined with the second surface 340 of the first substrate 306 and the first surface 342 of the second substrate 308 to produce a continuous length of elastomeric laminate 302. In addition, the bond applicator 500 may be configured to apply the bonds 322 before elastic laminate 302 advances from the first roller 324.

In some configurations, the speed S2 is less than the speed S1, and as such, the elastic strands 316 are stretched in the machine direction MD. With continued reference to FIG. 13, the second substrate 308 advances at speed S1 to the first roller 324 and partially wraps around the outer circumferential surface 326 of the first roller 324. In turn, the second substrate 308 is combined with the first substrate 306 and the stretched elastic strands 316 while on the first roller 324 such that the elastic strands 316 are joined with the second surface 340 of the first substrate 306 and the first surface 342 of the second substrate 308 to produce a continuous length of elastomeric laminate 302. In addition, the bond applicator 500 may be configured to apply the bonds 322 before elastic laminate 302 advances from the first roller 324.

It is also to be appreciated that in some configurations, the first substrate and second substrate 306, 308 herein may be defined by two discrete substrates or may be defined by folded portions of a single substrate. For example, as shown in FIG. 14, the first substrate 306 advances at speed S1 to the first roller 324 where the first substrate 306 partially wraps around the outer circumferential surface 326 of the first roller 324. While partially wrapped around the outer circumferential surface 326 of the first roller 324, the first substrate 306 is combined with the elastic strands 316. As the beam 314 rotates, the elastic strands 316 advance from the beam 314 at a speed S2 with the elastic strands 316 being spaced apart from each other in the cross direction CD. From the beam 314, elastic strands 316 advance to the first roller 324 and are positioned on the second surface 340 of the first substrate 306. As shown in FIGS. 14 and 15, a folding device 368 may operate to fold a first portion 306a onto a second portion 306b of the first substrate with the elastic strands 316 positioned between the first and second portions 306a, 306b to create the elastic laminate 302. As shown in FIGS. 14 and 16, the bond applicator 500 may be configured to apply the bonds 322 before elastic laminate 302 advances from the first roller 324.

Figure 17:
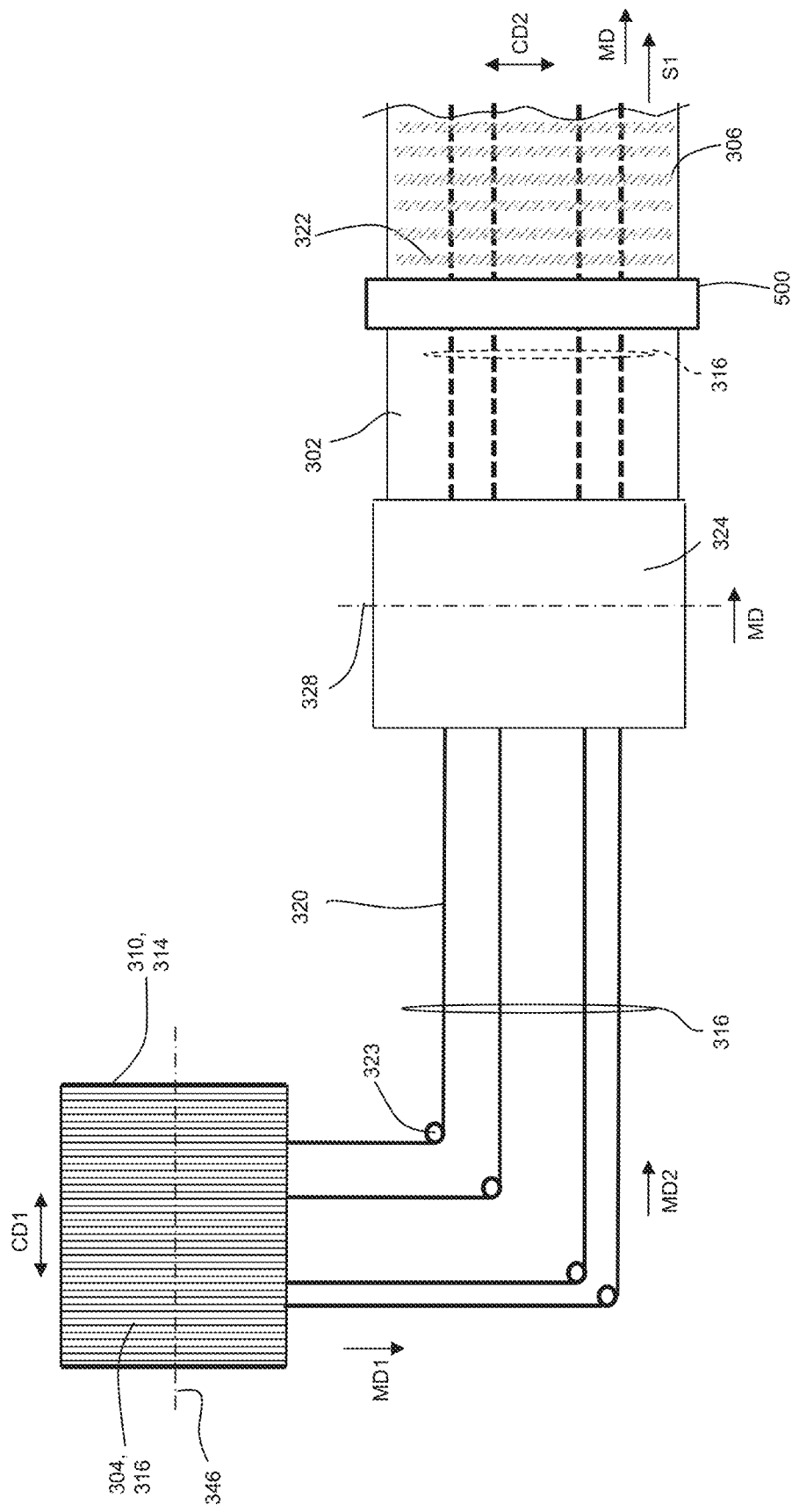
FIG. 17 is a schematic side view of a sixth configuration of a converting apparatus adapted to manufacture an elastomeric laminate.

As illustrated herein, the apparatuses and processes may be configured such that elastic strands may be advanced from the beams and directly to the assembly process without having to touch additional machine components, such as for example, guide rollers. It is also to be appreciated that in some configurations, elastic strands may be advanced from beams and may be redirected and/or otherwise touched by and/or redirected before advancing to the assembly process. For example, FIG. 17 shows a configuration where the beam rotation axis 346 may extend in a first cross direction CD1. As the beam 314 rotates, the elastic strands 316 advance from the beam 314 in a first machine direction MD1 with the elastic strands 316 being spaced apart from each other in the first cross direction CD1. The elastic strands 316 may then be redirected by rollers 323 from the first machine direction MD1 to a second machine direction MD2, wherein the elastic strands 316 may remain separated from each other in a second cross direction CD2. From the rollers 323, the elastic strands 316 may advance in the second machine direction MD2 to be combined with the first and second substrates 306, 308 to form the elastomeric laminate 302. Thus, it is to be appreciated that the beam 314 may be arranged and/or oriented such that the beam rotation axis 346 may be parallel, perpendicular, or otherwise angularly offset with respect to the machine direction advancement of the elastomeric laminate 302 and/or the substrates 306, 308.

It is to be appreciated that the bonding methods and apparatuses herein may be utilized in conjunction with other bonding methods and apparatuses and/or assemble various types of laminates and absorbent articles, such as disclosed in U.S. Patent Application Nos. 62/686,896, filed on Jun. 19, 2018; 62/687,031, filed on Jun. 19, 2018; 62/685,429, filed on Jun. 15, 2018; 62/581,278, filed on Nov. 3, 2017; 62/553,149, filed on Sep. 1, 2017; 62/553,538, filed on Sep. 1, 2017; and 62/553,171, filed on Sep. 1, 2017, and U.S. Patent Publication Nos. 2018/0168880A1; 2018/0170027A1; 2018/0169964A1; 2018/0168879A1; 2018/0170026A1; 2018/0168889A1; 2018/0168874A1; 2018/0168875A1; 2018/0168890A1; 2018/0168887A1; 2018/0168892A1; 2018/0168876A1; and 2018/0168891A1, the entireties of which are all incorporated by reference herein.

This application claims the benefit of U.S. Provisional Application Nos. 62/686,896, filed on Jun. 19, 2018; 62/687,031, filed on Jun. 19, 2018; 62/685,429, filed on Jun. 15, 2018; 62/581,278, filed on Nov. 3, 2017; 62/553,149, filed on Sep. 1, 2017; 62/553,538, filed on Sep. 1, 2017; and 62/553,171, filed on Sep. 1, 2017, the entireties of which are all incorporated herein by reference herein.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making absorbent articles, the method comprising steps of:
   rotating a pattern roll about an axis of rotation extending axially in a cross direction, the pattern roll comprising pattern elements extending radially outward from the axis of rotation;

providing a first roller and a second roller adjacent the first roller to define a nip between the first roller and the second roller;

advancing a first substrate and a second substrate through in a machine direction through the nip at a first speed S1 of at least about 100 meters per minute;

providing mandrel cores with at least one elastic strand wound onto each mandrel core;

rotating the mandrel cores and unwinding elastic strands from the mandrel cores;

advancing the elastic strands from the rotating mandrel cores;

stretching the elastic strands; and applying adhesive to at least one of the elastic strands, the first substrate, and the second substrate;

advancing the stretched elastic strands between the first substrate and the second substrate at the nip to form an elastomeric laminate; and intermittently engaging the elastomeric laminate with the pattern elements on the pattern roll.

2. The method of claim 1, wherein the first substrate comprises a first nonwoven and the second substrate comprises a second nonwoven, and wherein the elastic strands comprise a decitex of less than about 100.

3. The method of claim 1, wherein further comprising a step of spacing the elastic strands apart from each other by about 0.5 mm to about 4 mm.

4. The method of claim 1, wherein the elastic strands comprise about 200 to about 1000 elastic strands.

5. The method of claim 1, wherein the pattern elements extend in the cross direction for a length of at least about 100 mm.

6. The method of claim 5, further comprising a step of providing a pressing surface adjacent the pattern roll to define a second nip between the pattern roll and the pressing surface.

7. The method of claim 6, wherein the pressing surface comprises an energy transfer surface of an ultrasonic horn.

8. The method of claim 6, wherein at least one of the pattern roll and the pressing surface is heated.

9. The method of claim 1, wherein the step of stretching the elastic strands further comprises:

rotating the mandrel cores to unwind the elastic strands from the mandrel cores at a second speed S2, wherein S2 is less than S1.

10. The method of claim 1, wherein the elastic strands comprise a spin finish, and further comprising a step of removing a portion of the spin finish.

* * * * *